US009188554B2

(12) United States Patent
Shishido et al.

(10) Patent No.: US 9,188,554 B2
(45) Date of Patent: Nov. 17, 2015

(54) PATTERN INSPECTION DEVICE AND PATTERN INSPECTION METHOD

(71) Applicant: Hitachi High-Technologies Corporation, Tokyo (JP)

(72) Inventors: Chie Shishido, Tokyo (JP); Shinya Murakami, Tokyo (JP); Takashi Hiroi, Tokyo (JP); Taku Ninomiya, Tokyo (JP); Michio Nakano, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/403,668

(22) PCT Filed: May 22, 2013

(86) PCT No.: PCT/JP2013/064143
§ 371 (c)(1),
(2) Date: Nov. 25, 2014

(87) PCT Pub. No.: WO2013/179956
PCT Pub. Date: Dec. 5, 2013

(65) Prior Publication Data
US 2015/0212019 A1     Jul. 30, 2015

(30) Foreign Application Priority Data

May 28, 2012   (JP) ................................. 2012-120381

(51) Int. Cl.
*G01N 23/225*   (2006.01)
*G03F 1/86*   (2012.01)
(Continued)

(52) U.S. Cl.
CPC ............ *G01N 23/2251* (2013.01); *G01B 15/04* (2013.01); *G03F 7/7065* (2013.01);
(Continued)

(58) Field of Classification Search
USPC ............ 250/306, 307, 310, 311, 370.08, 582, 250/583, 585, 492.1, 492.2, 492.3, 526; 382/141, 144, 145, 149, 217, 276, 325
See application file for complete search history.

(56) References Cited

U.S. PATENT DOCUMENTS

| | | | | |
|---|---|---|---|---|
| 2010/0158345 | A1* | 6/2010 | Kitamura | G06T 7/0006 382/145 |
| 2011/0311126 | A1* | 12/2011 | Sakai | G01N 21/47 382/149 |

FOREIGN PATENT DOCUMENTS

| | | |
|---|---|---|
| JP | 2004-109788 A | 4/2004 |
| JP | 2006-11270 A | 1/2006 |

(Continued)

*Primary Examiner* — Bernard E Souw
(74) *Attorney, Agent, or Firm* — Baker Botts L.L.P.

(57) ABSTRACT

Provided is a pattern inspection device for accurately simulating an electron beam image of a circuit pattern on a wafer from design data, and implementing high-precision defect detection based on the comparison between the simulated electron beam image and a real image. A pattern inspection device comprises: an image capturing unit for capturing an electron beam image of a pattern formed on a substrate; a simulated electron beam image generation unit for generating a simulated electron beam image using a parameter indicating the characteristics of the electron beam image on the basis of design data; and an inspection unit for comparing the electron beam image of the pattern, which is the image captured by the image capturing unit, and the simulated electron beam image generated by the simulated electron beam image generation unit, and inspecting the pattern on the substrate.

18 Claims, 34 Drawing Sheets

(51) Int. Cl.
*G06K 9/00* (2006.01)
*G01B 15/04* (2006.01)
*G03F 7/20* (2006.01)
*H01J 37/22* (2006.01)
*H01J 37/28* (2006.01)

(52) U.S. Cl.
CPC ............... *H01J37/222* (2013.01); *H01J 37/28* (2013.01); *H01J 2237/2806* (2013.01); *H01J 2237/2817* (2013.01)

(56) References Cited

FOREIGN PATENT DOCUMENTS

| | | |
|---|---|---|
| JP | 2007-304959 A | 11/2007 |
| JP | 2011-23273 A | 2/2011 |
| JP | 2011-180066 A | 9/2011 |
| JP | 2011-191296 A | 9/2011 |
| JP | 2012-2663 A | 1/2012 |

* cited by examiner

FIG.4
(a)
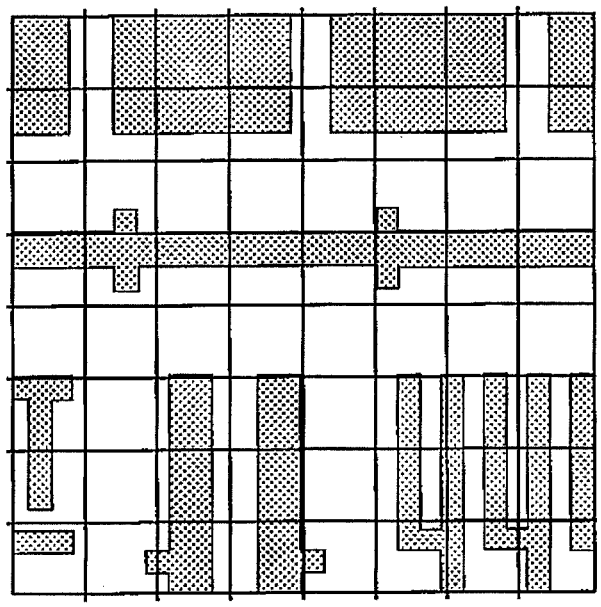
(b)
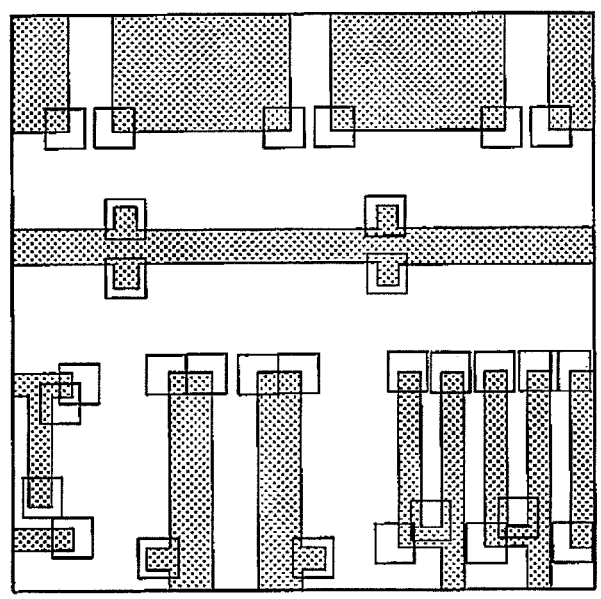

FIG.5
(a)
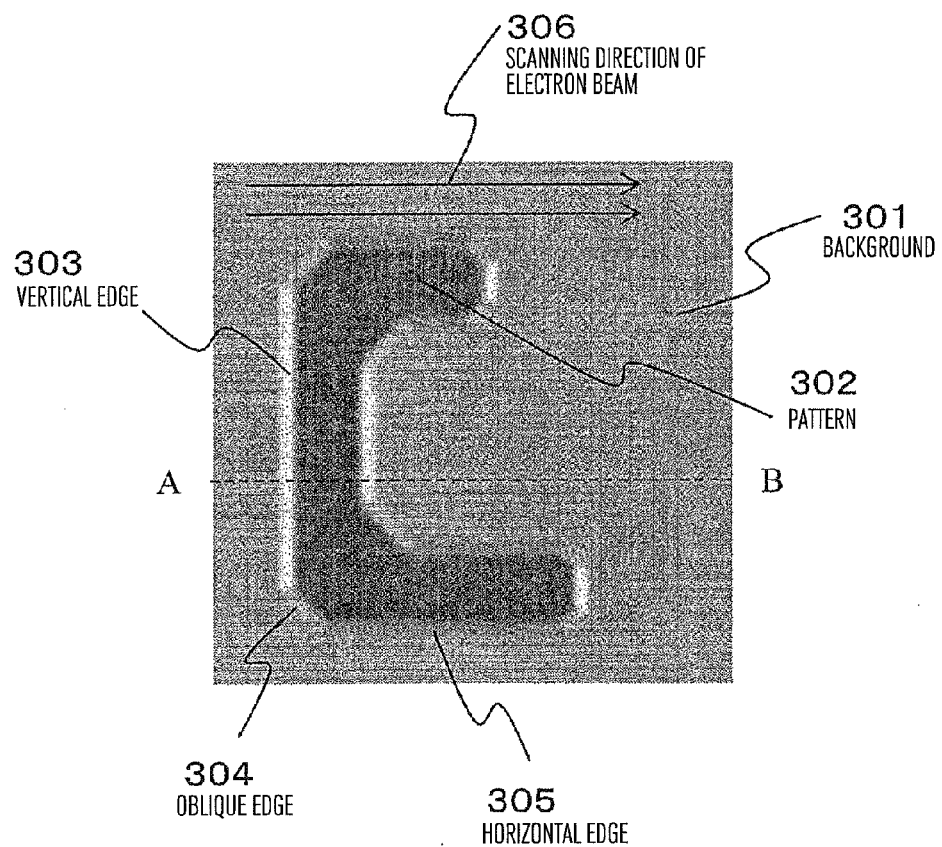
(b)
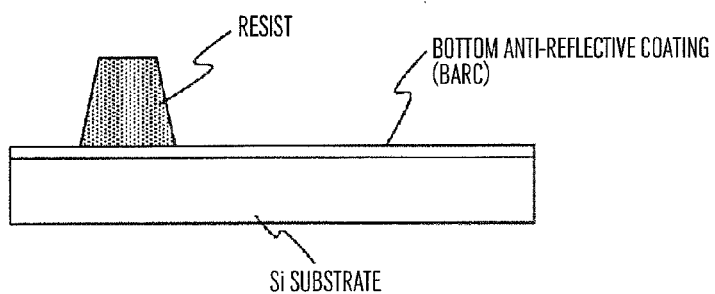

FIG.7
(a)
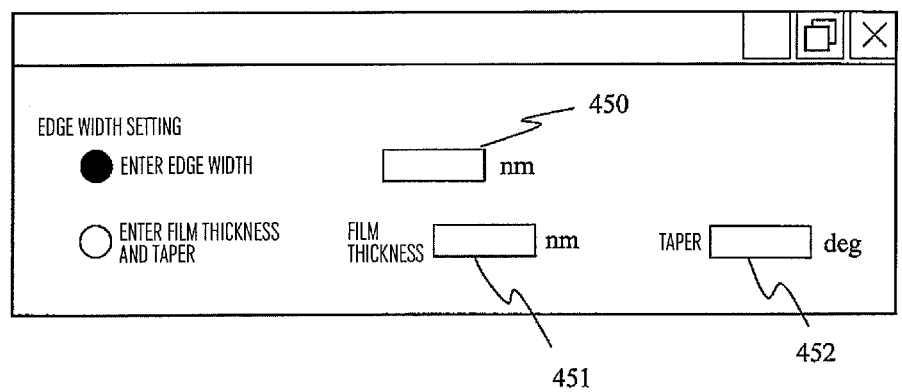
(b)
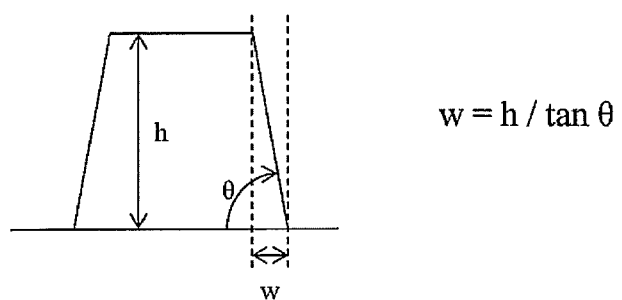
$w = h / \tan \theta$

FIG.11
(a)
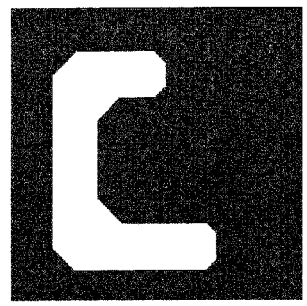
(b)
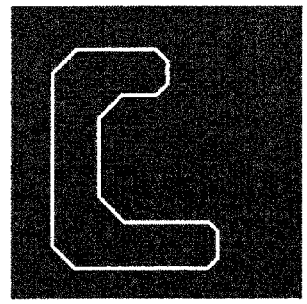
(c)
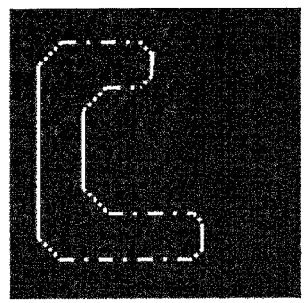
(d)
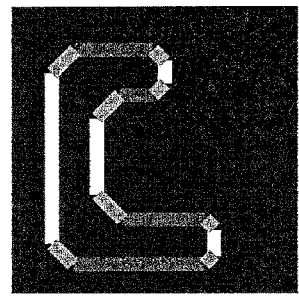
(e)
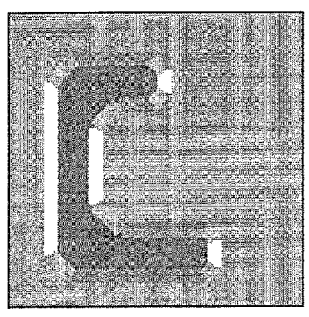
(f)
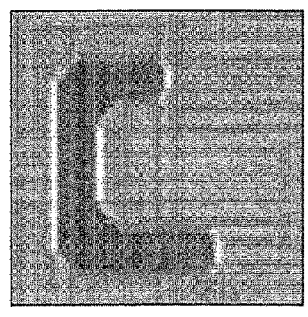

FIG.17
(a)
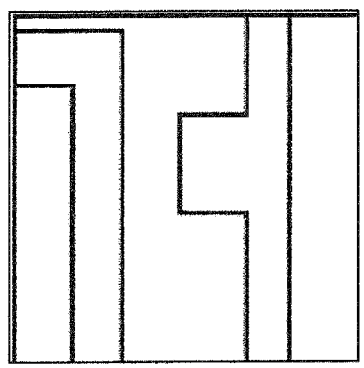
(b)
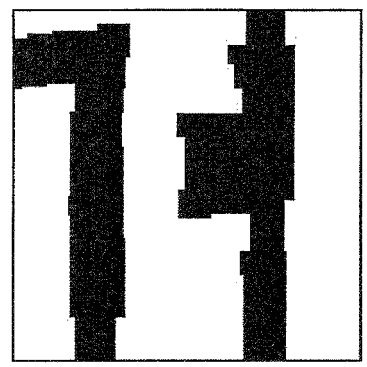
(c)
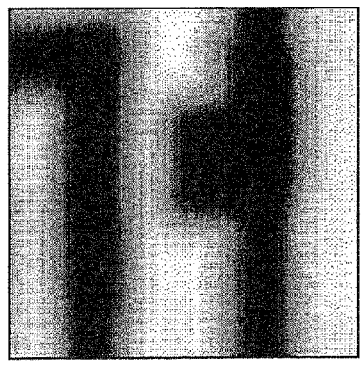
(d)
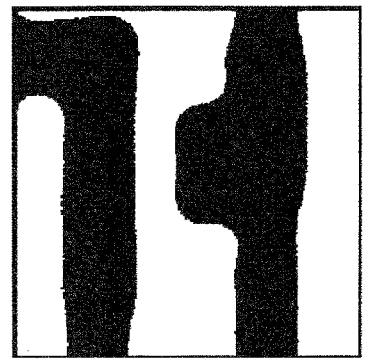

FIG.28
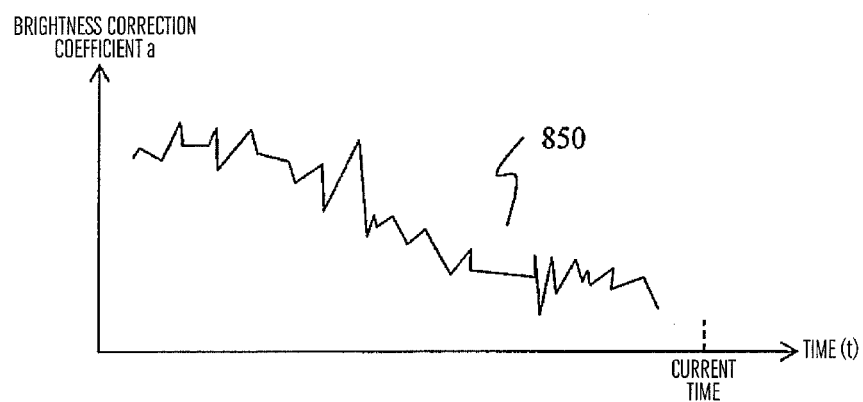
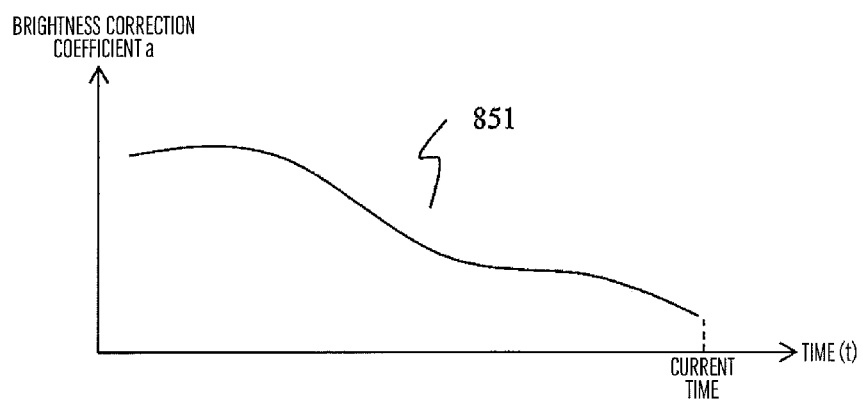

FIG.33
(a)
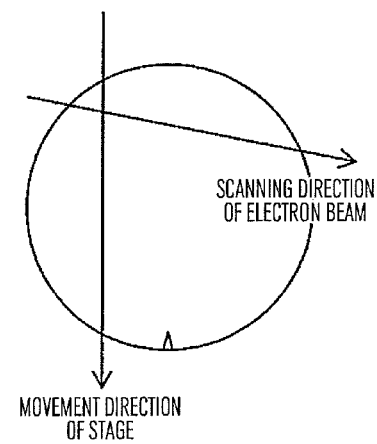
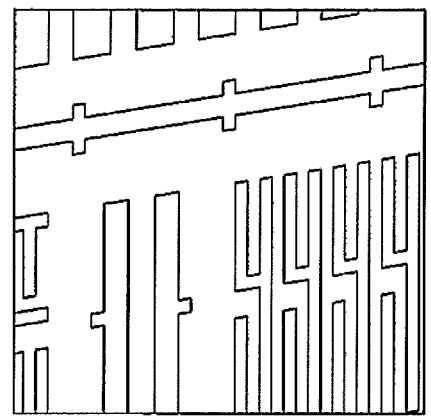
(b)
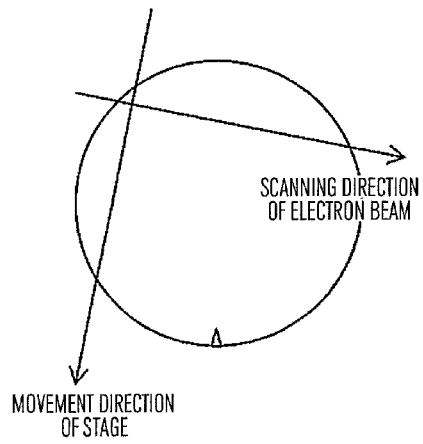
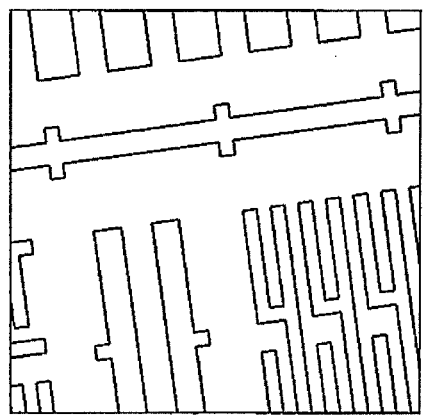

PATTERN INSPECTION DEVICE AND PATTERN INSPECTION METHOD

TECHNICAL FIELD

The present invention relates to a pattern inspection device and a pattern inspection method.

BACKGROUND ART

As a semiconductor circuit pattern becomes more and more miniaturized, the resolution of an exposure device is approaching the limit, making it more and more difficult to form a pattern on a wafer as designed. The generation frequency of systematic defects, such as a line width deviation from a design value or a deformed tip shape, increases. Because these systematic defects are generated in any of all dies, it is difficult to detect them in the conventional die-to-die (or abbreviated to D2D) inspection that compares between the data on the neighboring dies. Therefore, there is an increased need for the die-to-database (or abbreviated to D2DB) inspection that compares data on a die with design data.

For a comparison between various types of data such as between a real image and design data, JP-A-2006-11270 (Patent Literature 1) discloses "a method for generating an image, which is generated from design data by simulating an imaged real image, for use as a reference image".

CITATION LIST

Patent Literature

PATENT LITERATURE 1: JP-A-2006-11270

SUMMARY OF INVENTION

Technical Problem

Because the technology disclosed in Patent Literature 1 assumes an optical inspection for an exposure mask, the simulation method for a real image assumes the simulation of the optical image of an exposure mask. This literature describes in detail the method for reflecting the blur of an edge of an optical image onto a simulated image. However, the problem is that no consideration is paid for the bright difference between a pattern and a background and for the brightness difference in the edge direction; these brightness differences are the problems generated when inspecting a resist pattern on a wafer with the use of an electron beam type inspection device. Another problem is that no application is provided deriving various parameters that are necessary for generating a simulated image and that represent the characteristics of a real image.

It is an object of the present invention to provide a pattern inspection device and a pattern inspection method for accurately simulating the electron beam image of a resist pattern on a wafer from design data and for implementing high-accuracy defect detection by comparing the simulated data and the real image.

Solution to Problem

To solve the above problems, the configuration described in CLAIMS is used. The present application includes a plurality of means for solving the problems described above. One of them is as follows.

A pattern inspection device includes an imaging unit that images an electron beam image of a pattern formed on a substrate; a simulated electron beam image generation unit that generates a simulated electron beam image using a parameter based on design data, the parameter representing a characteristic of the electron beam image; and an inspection unit that inspects the pattern on the substrate by comparing the electron beam image of the pattern and the simulated electron beam image, the electron beam image of the pattern being imaged by said imaging unit, the simulated electron beam image being generated by said simulated electron beam image generation unit.

Advantageous Effects of Invention

According to the present invention, there is provided a pattern inspection device and a pattern inspection method for accurately simulating the electron beam image of a resist pattern on a wafer from design data and for implementing high-accuracy defect detection by comparing the simulated data and the real image.

BRIEF DESCRIPTION OF DRAWINGS

FIG. 4 is a diagram showing a method for detecting a positional deviation in the first embodiment of the present invention.

FIG. 5 is a diagram showing the characteristic of a SEM image in the first embodiment of the present invention.

FIG. 7 is a diagram showing a method for calculating parameters for generating a simulated SEM image in the first embodiment of the present invention.

FIG. 11 is a diagram showing an intermediate processing result in the simulated SEM image generation in the first embodiment of the present invention.

FIG. 17 is a diagram showing a variation in design data in a second embodiment of the embodiment of the present invention.

FIG. 28 is a diagram showing another calculation method for brightness correction coefficient in a ninth embodiment of the present invention.

FIG. 33 is a diagram showing a variation in electron beam scanning in a thirteenth embodiment of the present invention.

DESCRIPTION OF EMBODIMENTS

First Embodiment

Figure 1:
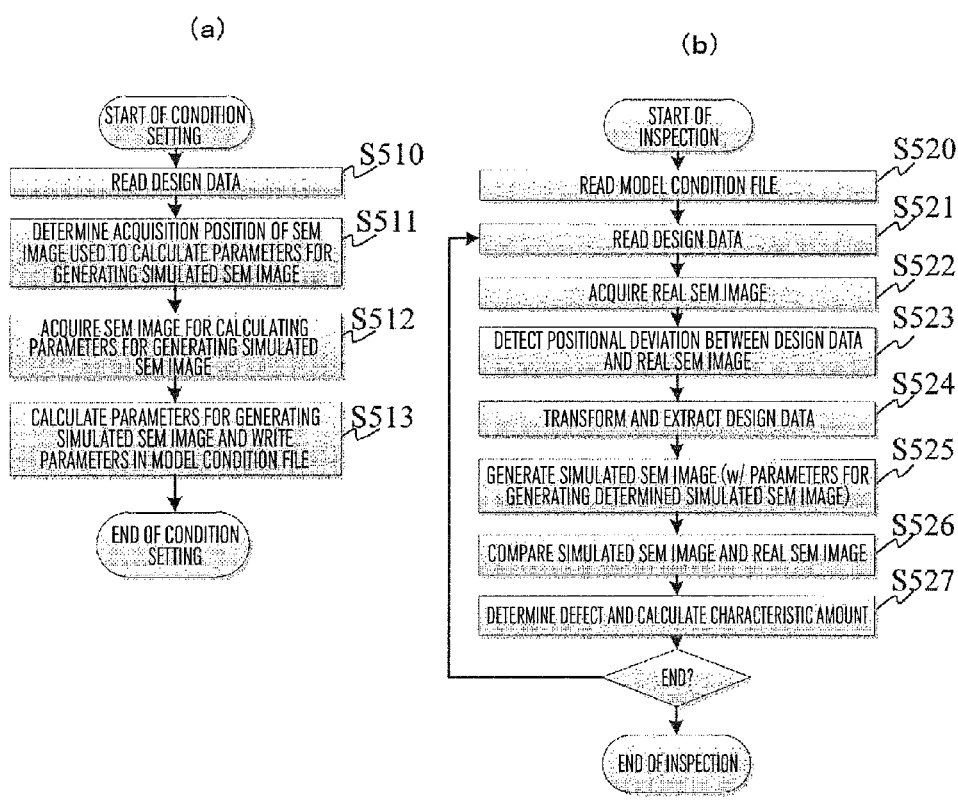
FIG. 1 is a diagram showing an overall flow in a first embodiment of the present invention.

The following describes an overall configuration of a first embodiment of the present invention, followed sequentially by the description of the content of each processing.
(1-1) Overall Flow First, with reference to FIG. 2, the overall configuration of a pattern inspection device according to the present invention is described.

In this embodiment, a wafer image to be inspected is acquired by a scanning electron microscope (SEM). An electron optics system 100 includes an electron source 101 that generates an electron beam, a condenser lens 102 that converges the electron beam, a deflector 103 that deflects the electron beam into the XY direction, an object lens 104, and an XY stage 105. A secondary electron 107 generated from a wafer 106 is detected by a detector 108, is converted from the analog signal to the digital signal by an A/D converter 109, is input to an image input unit 110, and is stored in a storage device 111.

An image to be inspected is one of the two types of image: continuous image and sheet image. A continuous image is obtained by the one-dimensional scanning of an electron beam and the continuous movement of the stage. A sheet image is obtained by the two-dimensional scanning of an electron beam and the step movement of the stage.

A sequence of inspection processing is performed by a system management unit 115 via a bus 114. Before the inspection, design data is stored in advance in a storage device 112. A design data calculation unit 113 converts the format of design data and selects a required portion, and an image processing unit 116 compares the design data and the above-mentioned inspection image for defect determination. The inspection result is output to a result output unit 117 and is stored in an inspection result storage unit 118.

FIG. 1 shows an overall flow. FIG. 1(a) shows a flow of condition setting performed before the inspection, and FIG. 1(b) shows a flow of inspection. In this embodiment, the design data and an inspection image are compared for defect determination as described above; in more detail, a simulated SEM image, which simulates the inspection image, is generated from design data, and this simulated SEM image is compared with the inspection image (real SEM image) for detecting a defect.

Before the inspection, various parameters, necessary for generating a simulated SEM image, are set during condition setting. First, the design data is read (S510), and the acquisition position on the real SEM image, used to calculate various parameters (pattern, background, edge brightness, blur amount of edges) necessary for generating the simulated SEM image, is determined on the design data (S511). After that, the real SEM image at that position is acquired (S512), the above parameters are calculated using a predetermined calculation method, and the calculated parameters are written in the condition file (S513). In the description below, this condition file is called a "model condition file" to distinguish this file from other files. The detail of step S511 and S512 will be described later.

At inspection time, the model condition file is read first (S520) and then the design data on a position, corresponding to an inspection area, is read (S521). After that, the real SEM image is acquired (S522) and a positional deviation between the design data and the real SEM image is detected (S523) and, based on the result, the design data is transformed and extracted (S524). Next, the simulated SEM image generation parameters, stored in the model condition file, are applied to the transformed/extracted design data to generate a simulated SEM image (S525). The obtained simulated SEM image and the real SEM image are compared (S526) for defect determination, and the coordinates of the defect portion and the defect size are output (S527). The steps from S521 to S527 are repeated until the inspection area is ended.
(1-2) Defect Determination Method The defect determination flow is described below with reference to FIG. 3 though a part of the description overlaps with the description of FIG. 1(b) given above. This flow is executed by the image processing unit 116 in FIG. 1.

First, the SEM image stored in the storage device 111 in FIG. 1 and the design data stored in the storage device 112 are read into the image processing unit 116 via the bus 114 (S202, S201). At this time, considering a deviation in the image acquisition position of the SEM image, design data 204 on an area larger than a SEM image 203 is read.

Next, the positional deviation between the design data and the SEM image is detected (S205). The specific method for detecting a positional deviation will be described in (1-3). Because the SEM image includes an image distortion caused by the scanning distortion of the electron beam or by a vibration in the stage, the positional deviation amount is not uniform in the image but is different among the points in the image. Therefore, the output is a positional deviation map 206 that indicates a deviation amount (Δx, Δy) for each position (x, y). After the design data is transformed based on the positional deviation map 206, the area corresponding to the SEM image is extracted (S207). After that, a simulated SEM image 209, which simulates the SEM image, is generated from the selected design data (S208). The method for generating a simulated SEM image will be described in (1-4), (1-5), (1-6), (1-7), and (1-8). A defect is determined by comparing the simulated SEM image 209 and the SEM image 203 (S210). Basically, a portion, where the shade difference between the two is higher than a predetermined threshold TH as indicated by expression (1), is determined as a defect, where the real SEM image is represented by f(x, y) and the simulated SEM image by g(x, y).

(MATH. 1)

$$|f(x,y)-g(x,y)|>TH \quad (1)$$

According to this embodiment, because comparison is performed using a non-defective simulated SEM image, a defect can be detected even if it is generated in any of the dies and cannot be detected by the traditional D2D inspection. In addition, in the D2D inspection, the post-processing is required to determine whether the defect is included in the inspection target f(x, y) or in the reference image g(x, y). Such post-processing is not required in this embodiment. In addition, a defect is determined based on the shade difference in this embodiment. Therefore, not only a defect caused by a change in the geometrical shape but also a defect generated due to a difference in image brightness, such as the one caused by a remnant resist film, can be detected.

Various technologies for increasing the inspection performance of shaded-image comparison may also be applied. These technologies include the local perturbation method, which is a method for detecting a defect through alignment on a local area basis, and the method that allows for a small shade difference caused by a positional deviation, equal to or smaller than a pixel, between the images to be compared.

As a defect determination result, the position coordinates of a defective portion 211, as well as the characteristic amounts such as the defect size or shade value of the defective portion, are output (S212).

(1-3) Positional Deviation Detection and Distortion Correction

Figure 3:
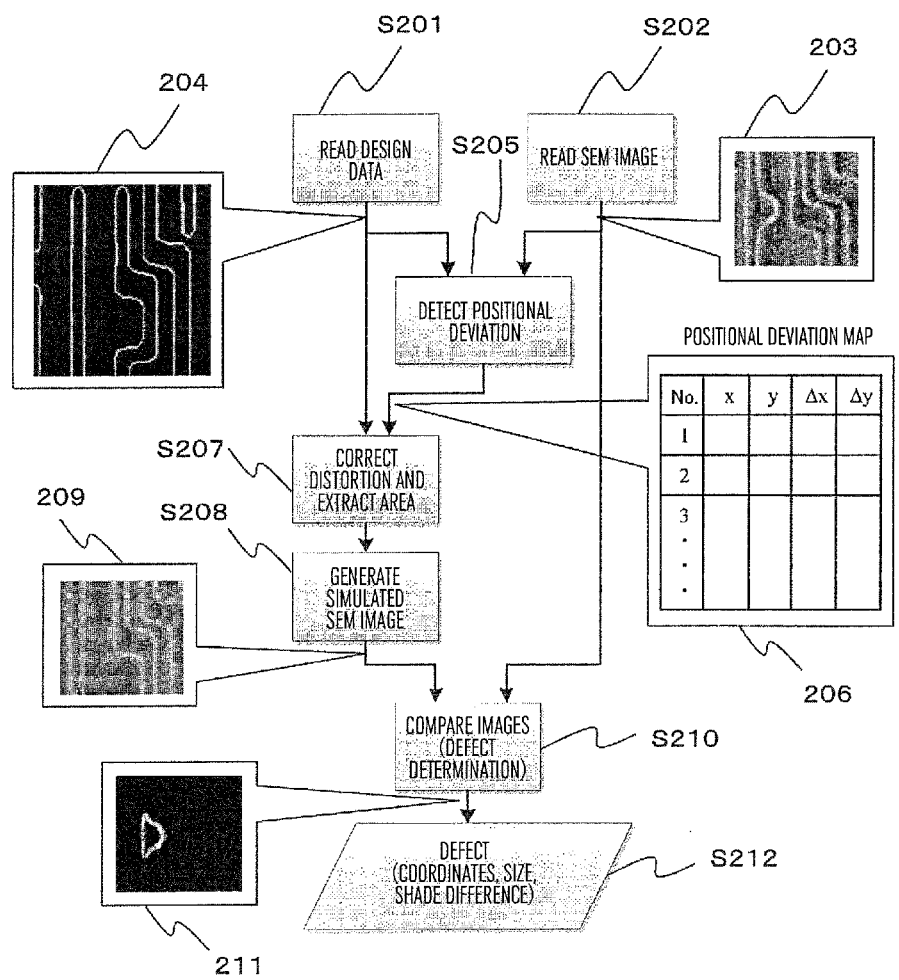
FIG. 3 is a diagram showing a flow of shade comparison in the first embodiment of the present invention.

Next, the method for detecting a positional deviation between the design data 204 and the SEM image 203, which is executed in step S523 in FIG. 1 or step S205 in FIG. 3, and distortion correction/extraction, which is executed in step S524 in FIG. 1 or step S207 in FIG. 3, are described.

Because the SEM image includes the scanning distortion of the electron beam or an image distortion caused by a vibration in the stage as described above, the positional deviation amount for the design data is not uniform in the image but is different among the points in the image. To detect this positional deviation amount, the image is divided into small meshes as shown in FIG. 4(a) to calculate the positional deviation amount in each mesh, or the positional deviation amount is calculated at a point (an area surrounded by a rectangle in the figure), such as a corner of a pattern shown in FIG. 4(b), where the positional deviation amount is determined uniquely. It is desirable that the positional deviation detection points, such as those shown in FIG. 4(b), be automatically selected using the design data before the inspection.

The positional deviation amount between the SEM image and the design data is detected as follows. First, a small area of the design data is relatively moved to a small area of the SEM image (each mesh in FIG. 4(a) and an area surrounded by a small square in FIG. 4(b)) and then the movement amount that minimizes the sum of squares of the difference between the two is calculated. Instead of the sum of squares of the difference, the movement amount, which maximizes the correlation coefficient between the two, may also be calculated. The positional deviation amount is calculated at an equal interval in FIG. 4(a), and at an unequal interval in FIG. 4(b). In either case, the positional deviation amount is defined at the representative coordinate points in the image. By interpolating the positional deviation amount at the representative coordinate points, the positional deviation amount at all coordinates is calculated. The positional deviation map 206, shown in FIG. 3, includes the thus-calculated positional deviation amount (Δx, Δy) of the design data corresponding to each pixel (x, y) of the real SEM image. In step S207 in FIG. 3, the design data corresponding to each pixel of the SEM image is selected according to the positional deviation map. By performing the processing described above, the design data, which locally matches the real SEM image in position (that is, deformed similarly), can be obtained.

According to this embodiment, instead of correcting a distortion to make the image match the design data, the design data is distorted to make the design data match the image. This method prevents uneven image deteriorations that may be caused by distorting the image, thus providing the advantage in detecting a defect.

(1-4) Modelling of Simulated SEM Image Generation

Next, the generation of the simulated SEM image, which is performed in step S525 in FIG. 1 or in step S208 in FIG. 3, is described. FIG. 5 schematically shows the characteristic of a SEM image. FIG. 5(b) is a cross section taken along line A-B. As shown in the figure, the SEM image of a resist pattern formed on a wafer is inspected in the first embodiment. A SEM image has the following characteristic.

(1) The edge portion (303, 304, 305) is brighter than the flat portion (301, 302). This is due to a tilt angle effect or an edge effect; this is a general characteristic of a secondary electron image.

(2) In general, the pattern portion (302) and the background portion (301) are different in brightness. The brightness of each portion depends on the material or the imaging condition.

(3) The brightness of an edge portion depends on the direction of the edge. This is the effect of the charging state of a sample. In many cases, an edge parallel to the scanning direction of the electron beam is darker than an edge vertical to the scanning direction as shown in FIG. 5(a). (In this example in which a scanning direction 306 of the electron beam is the horizontal direction, a horizontal-direction edge 305 is darker than a vertical-direction edge 303. An oblique edge 304 is intermediate in brightness).

Figure 6:
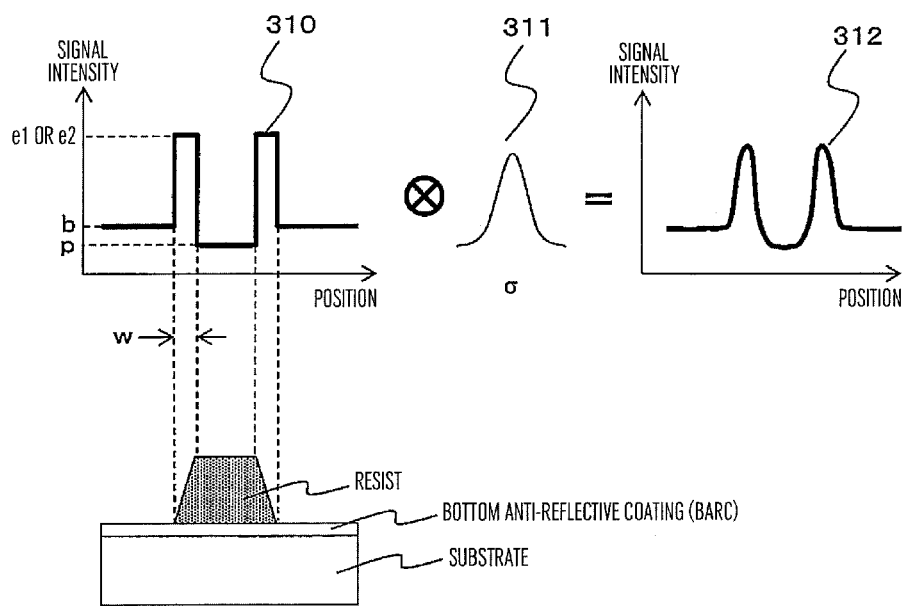
FIG. 6 is a diagram showing a method for modeling a SEM image in the first embodiment of the present invention.

To generate a simulated SEM image, on which the above-described characteristic of the SEM image is reflected, from the design data, a SEM image is modeled as shown in FIG. 6. The signal intensities e, b, and p are given to the design data, which is the line drawing (vector data) such as the one shown by the reference numeral 204 in FIG. 3, in the order of the signal intensity of the edge portion, background portion, and pattern portion as shown in 310. In more detail, to reproduce the characteristic described in (3) above, the signal intensity ev is given to the vertical-direction edge, and the signal intensity eh to the horizontal-direction edge. In addition, the edge width w is given. The blur of the edge portion, similar to that of the real image, is reproduced by convoluting a blur function 311, corresponding to the illumination beam intensity distribution, into a signal 310 (312). For example, the Gaussian function is used as the function representing the beam intensity distribution. In the modeling described above, the SEM image is simulated by the six parameters, that is, the signal intensities ev, eh, b, and p, edge width w, and beam size σ. It is desirable that these parameters be determined before the inspection such that they match the real SEM image. The specific calculation method for the parameters will be described in (1-5) and the subsequent parts.

The Monte Carlo simulation, which receives the cross section shape of the resist pattern as the input information, may also be used as a method for generating a simulated SEM image. However, this method is not practical when the inspection area is large because it requires a huge amount of calculation time. The simulated SEM image generation method described above, simple and speedy in processing, can generate a simulated SEM image in synchronization with the input of an image even in an inspection in which continuous images, obtained by the continuous movement of the stage, are processed.

(1-5) Calculation Method of Simulated SEM Image Generation Parameters

As described above, the parameters necessary for generating a simulated SEM image in this embodiment are the following six parameters: signal intensities ev, eh, b, and p, edge width w, and beam size σ. The determination method for these parameters is described below one by one.

FIG. 7 shows the determination method for the edge width w. As shown in FIG. 7(a), the user may enter a value 450 itself, or may enter a film thickness 451 and a taper angle 452, as the edge width. If there is a portion in the real SEM image where the edge width largely differs from the value, that portion is detected as a defect.

Figure 8:
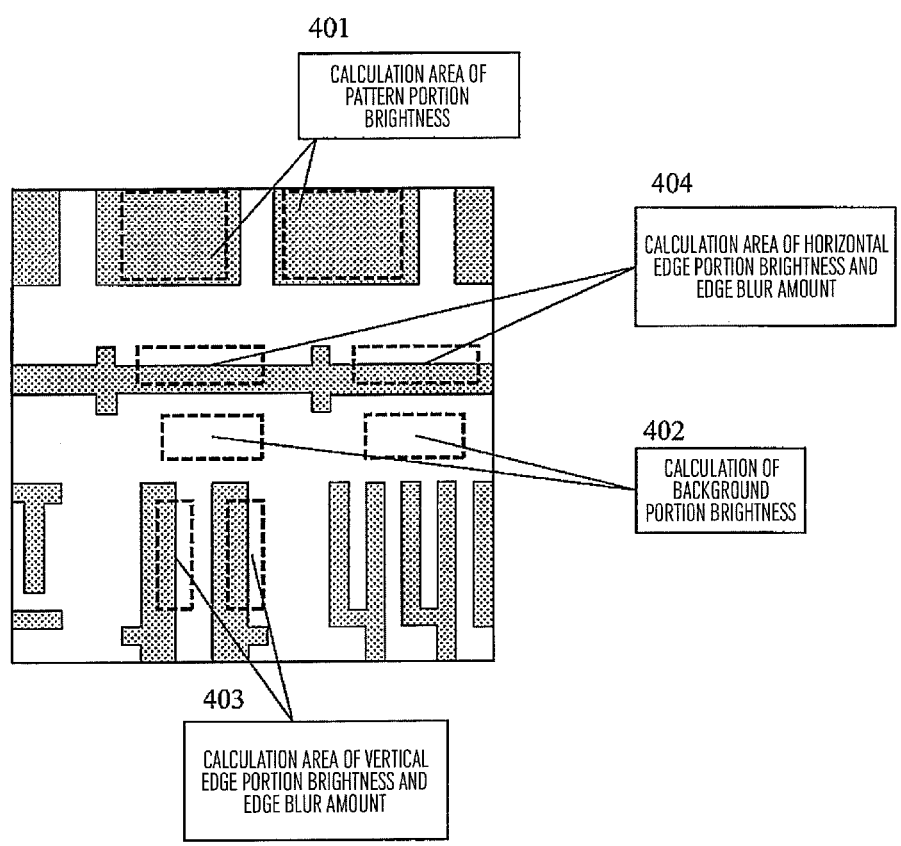
FIG. 8 is a diagram showing a method for calculating parameters for generating a simulated SEM image in the first embodiment of the present invention.

The signal intensity p of the pattern and the signal intensity b of the background are calculated from the real SEM image. FIG. 8 shows a part of the design data. The signal intensity p of the pattern is the average value of the brightness of the real SEM image corresponding to a wide pattern area 401. The signal intensity b of the background is the average value of the brightness of the real SEM image corresponding to a wide background area 402.

The signal intensities ev and eh of an edge portion, as well as the beam size σ, are calculated from the real SEM image. To calculate the vertical-direction signal intensity ev, a real SEM image that corresponds to an area 403, in which the vertical edge continues for a predetermined length and the pattern size is relatively large, is used. To calculate the horizontal-direction edge intensity eh, a real SEM image that corresponds to an area 404, in which the horizontal edge continues for a predetermined length and the pattern size is relatively large, is used.

Figure 9:
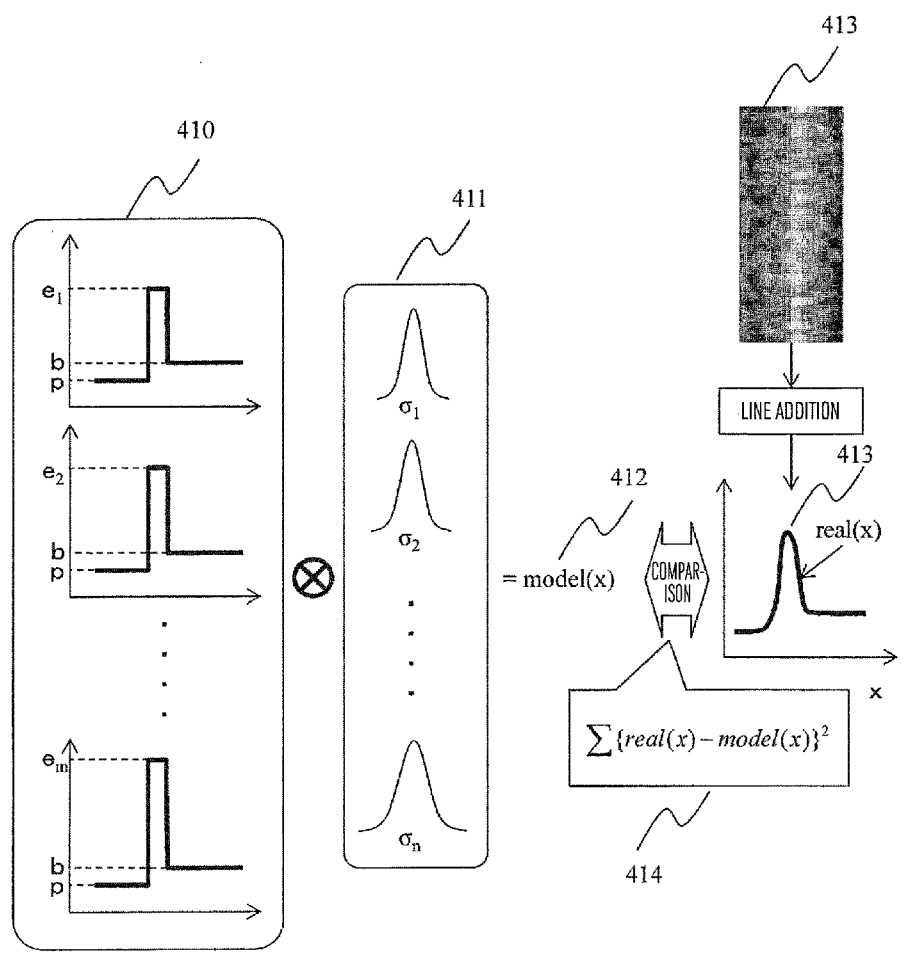
FIG. 9 is a diagram showing a method for calculating parameters for generating a simulated SEM image in the first embodiment of the present invention.

FIG. 9 shows the calculation method for the signal intensity (ev or eh) of an edge portion and the beam size σ. In the description below, it is assumed that the values of p and b are already determined. Signal waveforms 410, which include different signal intensities (e1-em) of the edge portion as indicated by the reference numeral 410, and (σ1-σn) Gaussian functions 411, which represent different σ values, are calculated in advance, and the functions 411 are convoluted into the signal waveforms 410. Let model(x) be the result (412). There are m×n results of model (x) in total. On the other hand, the real signal waveform real (x) is obtained from a real SEM image 413 (corresponding to the area 403 in FIG. 8). After that, the signal intensity and the beam size of the edge portion are determined such that the sum of squares of the differences between model(x) and real(x), calculated by expression (2), is minimized (414).

(MATH. 2)

$$\Sigma\{real(x) - model(x)\}^2 \qquad (2)$$

The same calculation method is used though ev uses the vertical edge of the real SEM image and eh uses the horizontal edge portion of the real SEM image. Instead using the round robin of a combination of n×m, it is also possible to specify an initial value and then recursively perform the calculation using the steepest descent method, Gauss-Newton method, or Levenberg-Marquardt method.

Because the brightness of the real SEM image differs between the vertical edge and the horizontal edge as described in (1-4) above, it is important to set parameter values separately as described above. In addition to the vertical/horizontal edge, the real pattern includes an oblique edge. The processing for an oblique edge is described in (1-6).

(1-6) Image Processing Flow of Simulated SEM Image Generation

Figure 10:
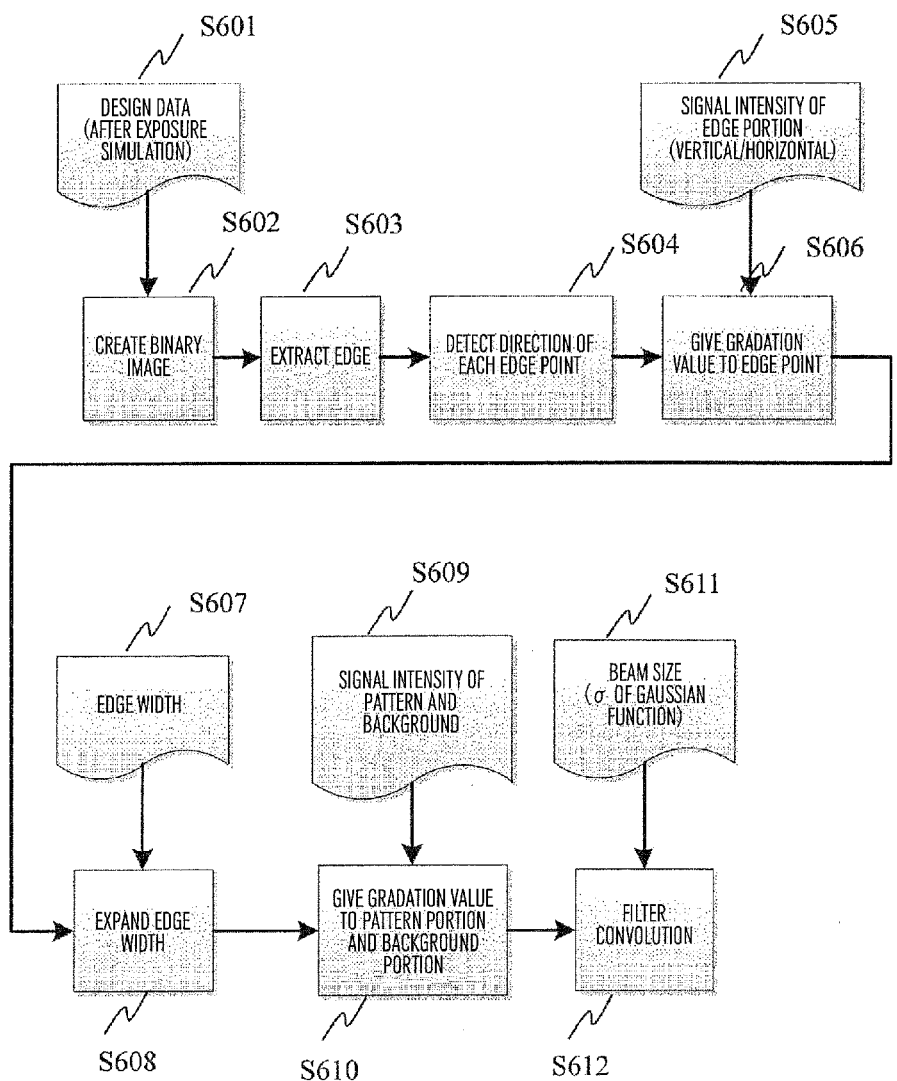
FIG. 10 is a diagram showing a flow of simulated SEM image generation processing in the first embodiment of the present invention.
Figure 12:
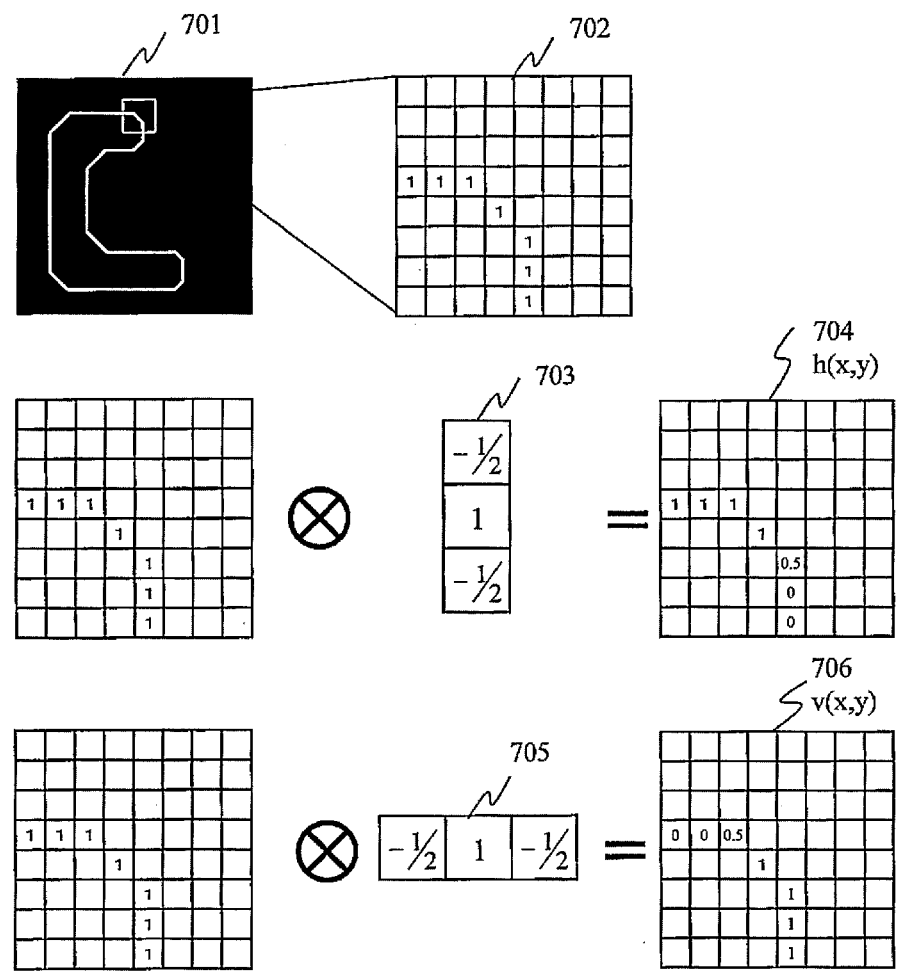
FIG. 12 is a diagram showing a method for calculating an edge direction in the simulated SEM image generation in the first embodiment of the present invention.

With reference to FIG. 10 to FIG. 12, the image processing flow of a simulated SEM image is described below. In this processing, the simulated SEM image generation parameters (signal intensities ev, eh, b, and p, edge width w, and beam size σ.), determined in the description above, are used. The following describes the steps in FIG. 10, one step at a time.

[Steps in FIG. 10]

S601: Receive the design data.

S602: Sample the data with a predetermined pixel size and create a binary image where the pattern portion is represented by 1 and the background portion by 0 (FIG. 11(a)).

S603: Detect the edge of the binary image (FIG. 11(b)).

S604: Calculate the direction of each edge point. The specific method for calculating the edge direction is described with reference to FIG. 12. The reference numeral 701 indicates the image after the edge is detected in step S603, and the reference numeral 702 indicates the enlarged image. The convolution of a horizontal edge detection operator 703 into the enlarged image generates an image 704. This is represented as h(x, y). On the other hand, the convolution of a vertical edge detection operator 705 into the enlarged image generates an image 706. This is represented as v(x, y). h(x, y) represents the horizontal-direction edge intensity, while v(x, y) represents the vertical-direction edge intensity. The edge direction dir(x, y) of each pixel can be calculated by expression (3).

(MATH. 3)

$$dir(x,y) = \tan^{-1}\{v(x,y)/h(x,y)\} \qquad (3)$$

FIG. 11(c) schematically represents the edge-direction calculation result. The vertical edge is indicated by the solid line, the horizontal edge by the dashed line, and the oblique edge by the dotted line (in practice, the edges are not limited to vertical/horizontal/oblique edges but each point has an edge direction represented by a real number).

S605: Receive the signal intensities (vertical and horizontal) of the edge portion determined in FIG. 9.

S606: Give a gradation value to an edge point based on the edge direction calculated in S604 and the signal intensity of the edge portion (vertical direction: ev, horizontal direction eh) received in S605 (FIG. 11 (d)). More specifically, when the gradation value of an edge point is represented as edge(e, y), edge(e, y) is the length of a vector with the direction of dir(x, y) on an ellipse with the vertical diameter of ev and the horizontal diameter of eh. The simultaneous equation, represented by expressions (4) and (5), is solved for p and q, and the resulting p and q are substituted in expression (6) to find the gradation value edge(e, y).

[MATH. 4]

$$\frac{p^2}{eh^2} + \frac{q^2}{ev^2} = 1 \quad (4)$$

[MATH. 5]

$$q/p = \tan\{dir(x,y)\} \quad (5)$$

[MATH. 6]

$$edge(x,y) = \sqrt{p^2 + q^2} \quad (6)$$

S607: Receive the edge width w determined in FIG. 7.
S608: Expand the edge width on the image to the width w.
S609: Receive the signal intensity p of the pattern portion and the signal intensity b of the background portion determined in FIG. 8.
S610: Give the gradation value p and the gradation value b, respectively, to the pattern portion and the background portion on the image (FIG. 11(e)).
S611: Receive the beam size (σ of Gaussian function) calculated in FIG. 9.
S612: Convolute the Gaussian function into the image obtained in S610 (FIG. 11(f)).

The content of processing in step 526 in FIG. 1(b) or in step S208 in FIG. 3 is as described above. According to this embodiment, a simulated SEM image, which is used for comparison with the real SEM image, can be generated from the design data using the simulated SEM image generation parameters calculated in advance.

Figure 13:
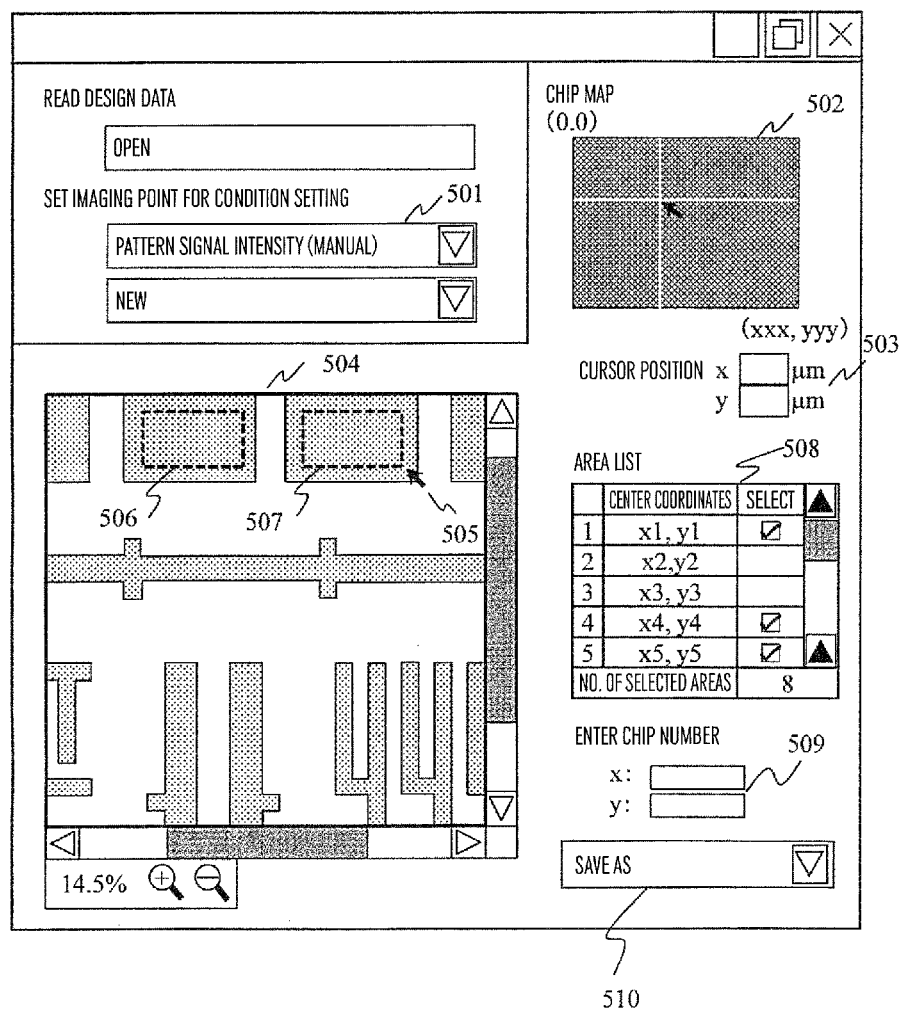
FIG. 13 is a diagram showing an example of a GUI screen for setting simulated SEM image generation parameters in the first embodiment of the present invention.
Figure 14:
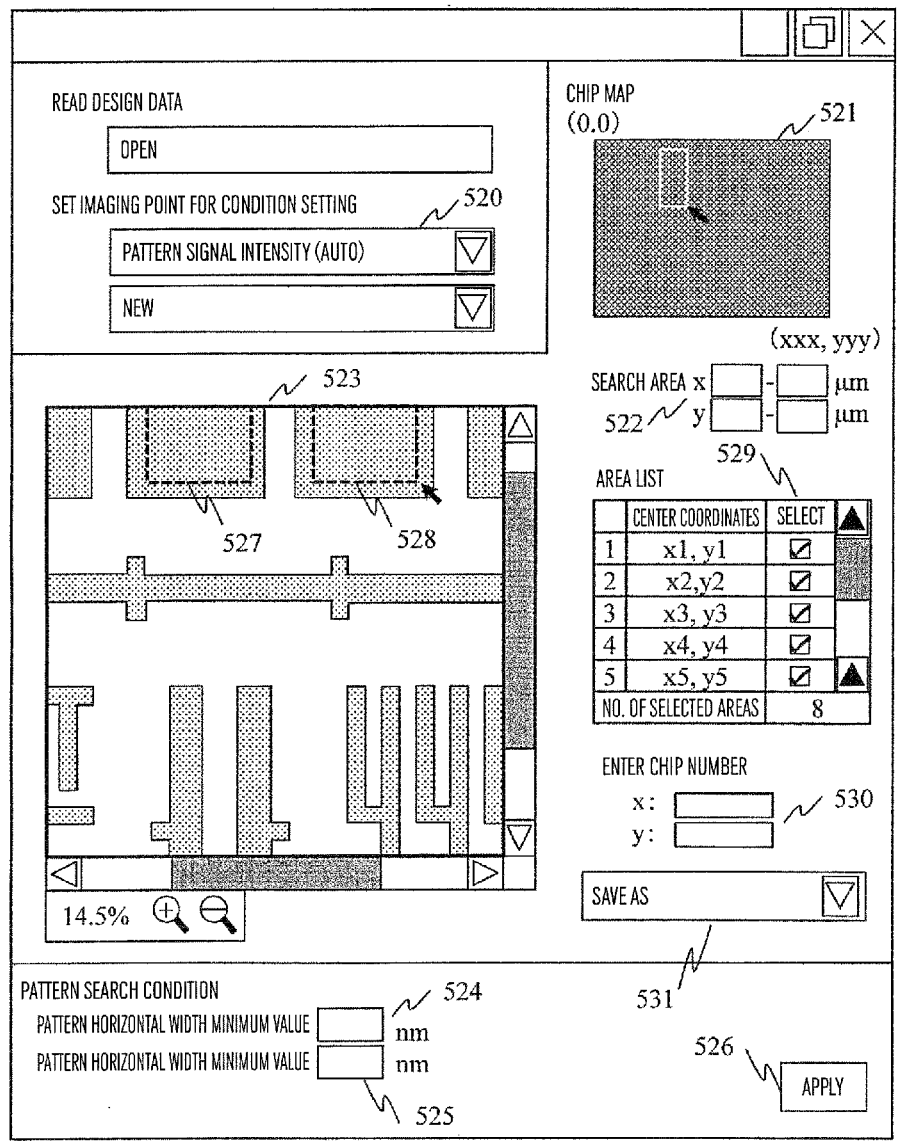
FIG. 14 is a diagram showing another example of a GUI screen for setting simulated SEM image generation parameters in the first embodiment of the present invention.
Figure 15:
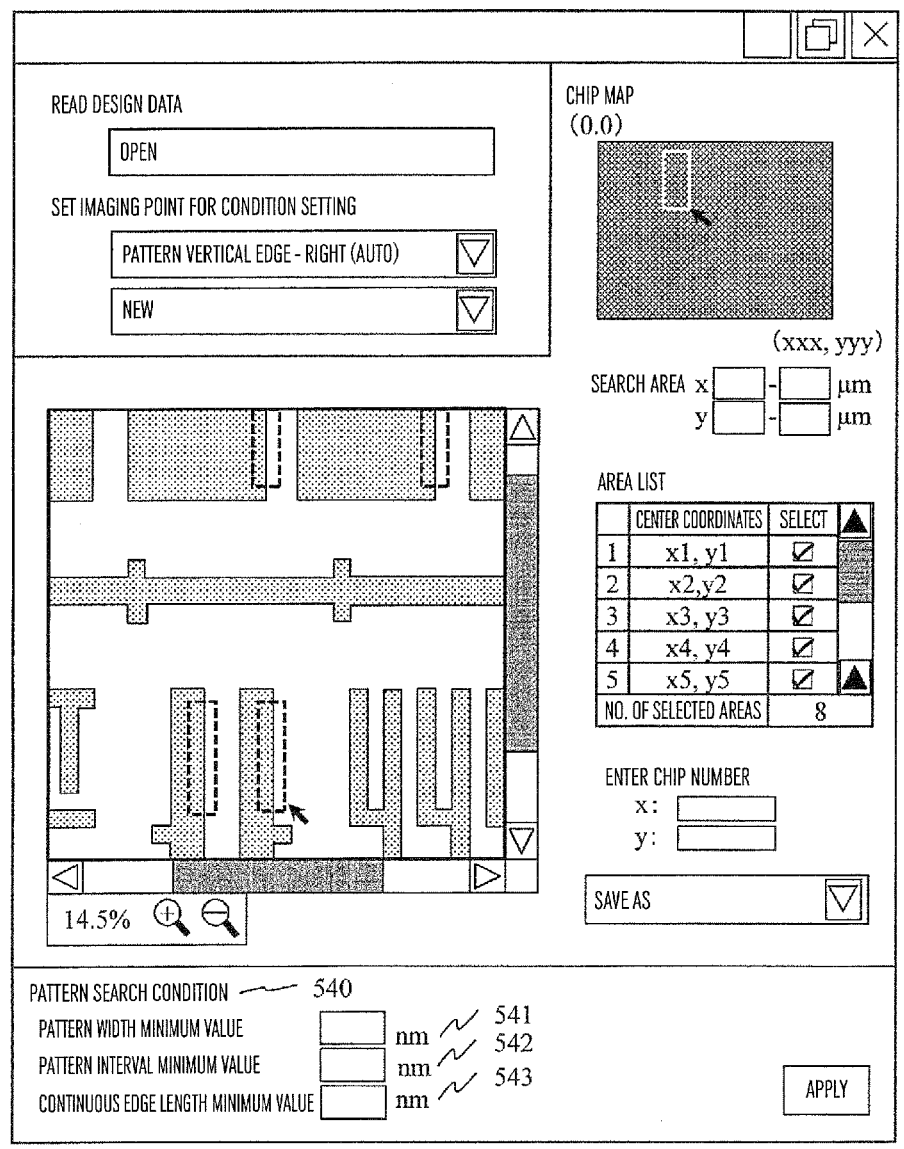
FIG. 15 is a diagram showing a still another example of a GUI screen for setting simulated SEM image generation parameters in the first embodiment of the present invention.

(1-7) Setting of Imaging Points of SEM Image for Calculating Simulated SEM Image Generation Parameters With reference to FIG. 13 to FIG. 15, the following describes steps S510 and S511 in FIG. 1(a), that is, the setting method of the imaging points of a real SEM image used for calculating the values of the simulated SEM image generation parameters.

FIG. 13 shows an example of the GUI screen for setting the imaging points of a SEM image for calculating the signal intensity p of a pattern portion. When "Manual" is selected in "Set imaging point for condition setting" 501, a chip map 502 is displayed, and design data 504 corresponding to the cursor position (503) on the chip map is displayed on the screen. On the design data, wide pattern areas 506 and 507, suitable for calculating the pattern portion signal intensity, are specified using a pointing device 505. The specified area is listed in an area list 508 as a candidate. After listing the areas, the whole or a part of the areas is specified (specified by the check mark), a chip number 509 is entered, and then it is saved as an imaging point information file (510). This method allows an imaging point to be determined offline without imaging the real SEM image.

FIG. 14 shows another example of the GUI screen for setting the imaging points of a SEM image for calculating the signal intensity p of a pattern portion. When "Auto" is selected in "Set imaging point for condition setting" 520, a chip map 521 is displayed. On this map, a search area is set with a pointing device or by entering a numeric value 522. Design data 523 corresponding to the area that is set is displayed on the screen. Because a wide pattern area is suitable for calculating the signal intensity of the pattern portion, a pattern horizontal width minimum value 524 and a pattern vertical width minimum value 525 are entered and an "Apply" 526 is clicked. Then, a pattern, which is included in the search area specified by the value 522 and whose vertical width and horizontal width are larger than those specified as the values 524 and 525, is automatically selected, is displayed on the design data on the screen (527, 528), and is listed in an area list 529 as a candidate. After listing the areas, the whole or a part of the areas is specified (specified by the check mark), a chip number 530 is entered, and then it is saved as an imaging point information file (531). To reliably find the signal intensity of the pattern portion, it is advantageous to specify more areas for calculating the average brightness of the areas. To set more areas, the method shown in FIG. 14 is more convenient than the method shown in FIG. 13.

FIG. 15 shows an example of the GUI screen for setting the imaging points of a SEM image for calculating the signal intensity of an edge portion. The screen configuration is similar to that in FIG. 11 except for a pattern search condition 540. While the minimum values of the vertical and horizontal widths of the pattern are entered in FIG. 11, a pattern width minimum value 541, a pattern interval minimum value 542, and a continuous edge length minimum value 543 are entered on this screen. This is because the wider the pattern width and the pattern interval and the longer the continuous edge length, the more reliably can the parameters, described in (1-5), be calculated. As in FIG. 14, the selected areas are listed in the area list.

Figure 16:
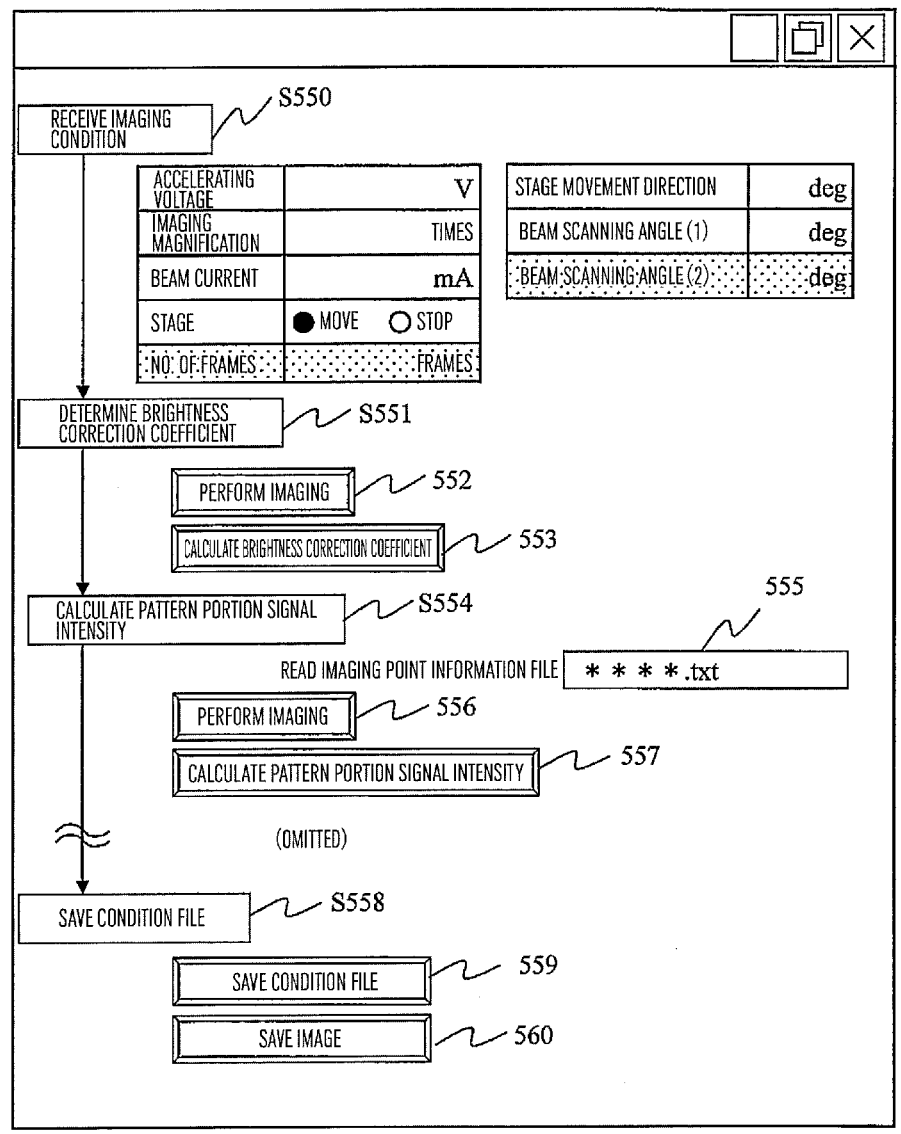
FIG. 16 is a diagram showing an example of a GUI screen for calculating simulated SEM image generation parameters in the first embodiment of the present invention.

(1-8) Imaging of SEM Image for Calculating Simulated SEM Image Generation Parameters With reference to FIG. 16, the following describes steps S512 and S513 in FIG. 1(a); that is, the following describes a sequence of processing in which the real SEM image for calculating the simulated SEM image generation parameters is imaged, the parameters are calculated using this real SEM image, and the result is saved.

FIG. 16 shows an example of the GUI screen for executing the sequence described above. First, an imaging condition is received (S550). In this step, the following are received: accelerating voltage, imaging magnification, beam current, whether the image is acquired by scanning the stage or acquired with the stage stopped, stage movement direction with respect to wafer, and beam scanning angle. The received content is written in the model condition file. Because a change in these imaging conditions involves a change in the image quality of the SEM image, it is necessary that the simulated SEM image generation parameters be linked to the imaging conditions and that the imaging condition at inspection time (FIG. 1(b)) be the same as the imaging condition received in S550. At inspection time, the model condition file is read and the same imaging condition is applied.

Next, the brightness correction coefficient is determined (S551). The brightness correction coefficient is a coefficient used for adjusting the gain and the offset for the output of the detector (108 in FIG. 1) so that the brightness of the real SEM image becomes proper. When the signal intensity before brightness correction is represented by i, the signal intensity after brightness correction is represented by j, the gain adjustment coefficient is represented by "gain", and the offset adjustment coefficient is represented by "offset", the following relation holds.

(MATH. 7)

$$j = \text{gain} \times i + \text{offset} \quad (7)$$

When a "Perform imaging" button 552 is clicked, imaging is performed in a suitable area in which both the pattern and the background are included. When "Calculate brightness correction coefficient" button 553 is clicked, the maximum value and the minimum value of the image brightness are calculated and "gain" and "offset" are calculated so that the maximum and minimum values become proper values. The calculation result of the brightness correction coefficient is written in the model condition file. Because a change in the brightness correction coefficient involves a change in the brightness of the SEM image, it is necessary that the simulated SEM image generation parameters be linked to the brightness correction coefficient and that the brightness correction coefficient at inspection time (FIG. 1(b)) be the same as the result calculated in S553. At inspection time, the model condition file is read and the same brightness correction coefficient is applied.

Next, the pattern portion signal intensity, one of the simulated SEM image generation parameters, is calculated (S554). Because the imaging point on the real SEM image for calculating the pattern portion signal intensity is already determined in step S511 in FIG. 1, the imaging point information file, in which the imaging point information is described, is specified in an area 555. When a "Perform imaging" button 556 is clicked, the real SEM image at the coordinates, described in the imaging point information file, is acquired under the imaging condition received in S550 and at the brightness coefficient determined in SS551. After that, when a "Calculate pattern signal intensity" button 557 is clicked, the pattern signal intensity (signal intensity of p indicated by the signal waveform 310 in FIG. 6) is calculated using the method described in FIG. 8. The calculation result is written in the model condition file.

The other simulated SEM image generation parameters, not shown, are calculated in the same manner, and these parameters are written also in the model condition file.

Finally, the condition file is saved (S558). When a "Save condition file" button 559 is clicked, the model condition file is saved with a desired file name. When a "Save image" button 560 is clicked, the image used in step S551 or step S554 is saved.

(1-9) Effect of the First Embodiment

According to the first embodiment described above, the inspection can be performed by comparing a real SEM image and a simulated SEM image. Although defects that are generated in any of all dies cannot be detected in the conventional D2D inspection, these defects can be detected in this embodiment. In addition, to generate a simulated SEM image, the parameters for generating the simulated SEM image must be determined accurately. To meet this requirement, this embodiment provides a specific parameter calculation method. In addition, this embodiment provides the parameter calculation support function that uses design data. This function allows the user of the inspection device to calculate the parameters easily and accurately. This generates a simulated SEM image still closer to the real SEM image, thus providing high inspection performance.

Second Embodiment

A second embodiment is an embodiment in which other types of design data are used. FIG. 17 shows the variations of design data. FIG. 17(a) shows a design intent, (b) shows a mask pattern, (c) shows a lithography simulation result with a mask pattern as its input, and (d) shows a contour line based on a lithography simulation result.

Although not specifically mentioned, (d) is used in the first embodiment. Of the remaining (a), (b), and (c), (c) represents multivalued data. The amount of multivalued data is so large that few inspection device users save the data of the whole inspection area in this format. Therefore, in the second embodiment, the case in which (a) is used and the case in which (b) is used are described. (d) has a shape similar to that of a real pattern on a wafer, while the deviation of (a) and (b) from a real pattern is so large that the preprocessing is required in each case to convert the shape.

Figure 18:
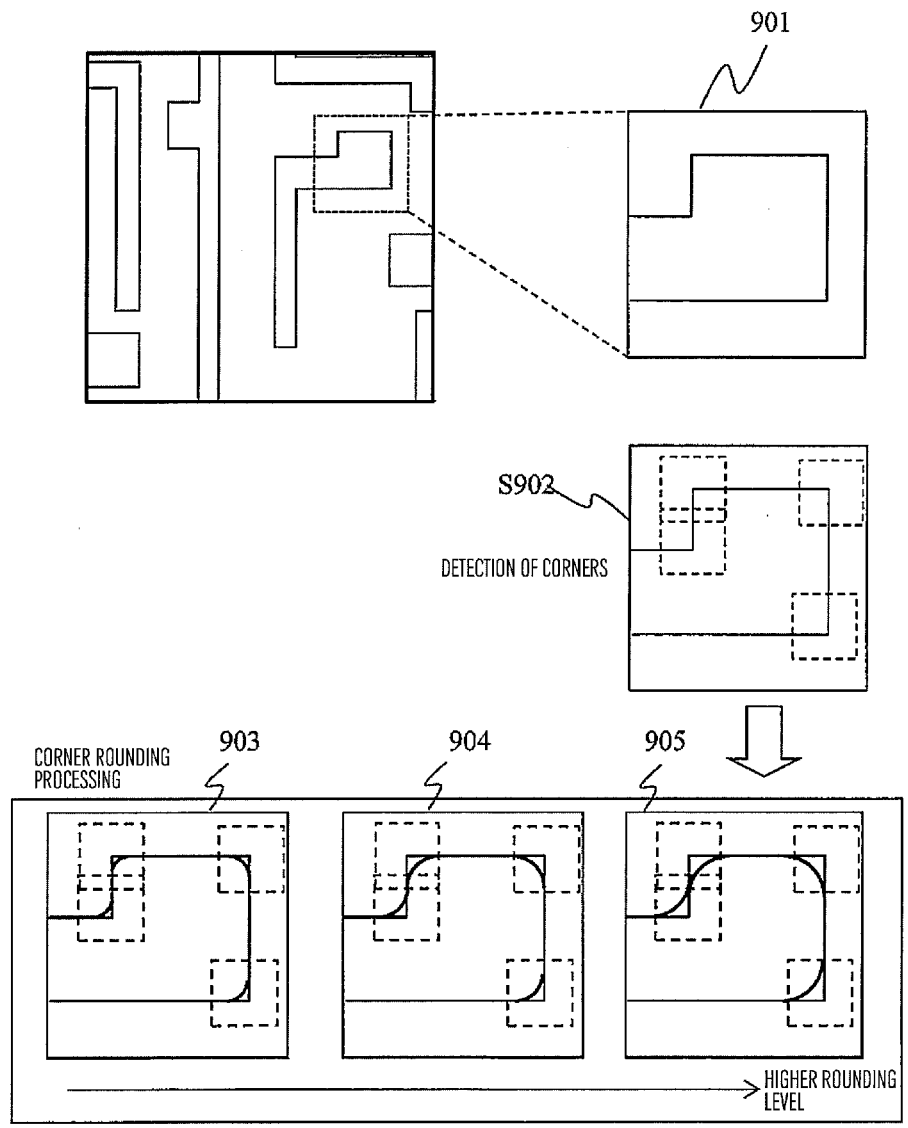
FIG. 18 is a diagram showing a design data conversion method when a design intent is used in the second embodiment of the present invention.

First, FIG. 18 shows the preprocessing that is performed when a design intent (FIG. 17(a)) is used. As indicated by the reference numeral 901, a design intent is generally configured by straight lines and has 90-degree corners. Because a corner of a pattern on the real wafer is round, the rounding of the corner is required as the preprocessing. The processing is performed in which the corners are detected from the intent design data (S902), a plurality of patterns (903-905) each having a different rounding intensity level are generated, and the rounding intensity is optimized by matching between each of the generated patterns and the real pattern. More specifically, the pattern with the maximum correlation coefficient between the real SEM image and the processed image is selected or the pattern is determined through visual observation. The rounding processing may be performed either at a time before the inspection or in synchronization with the inspection.

Figure 19:
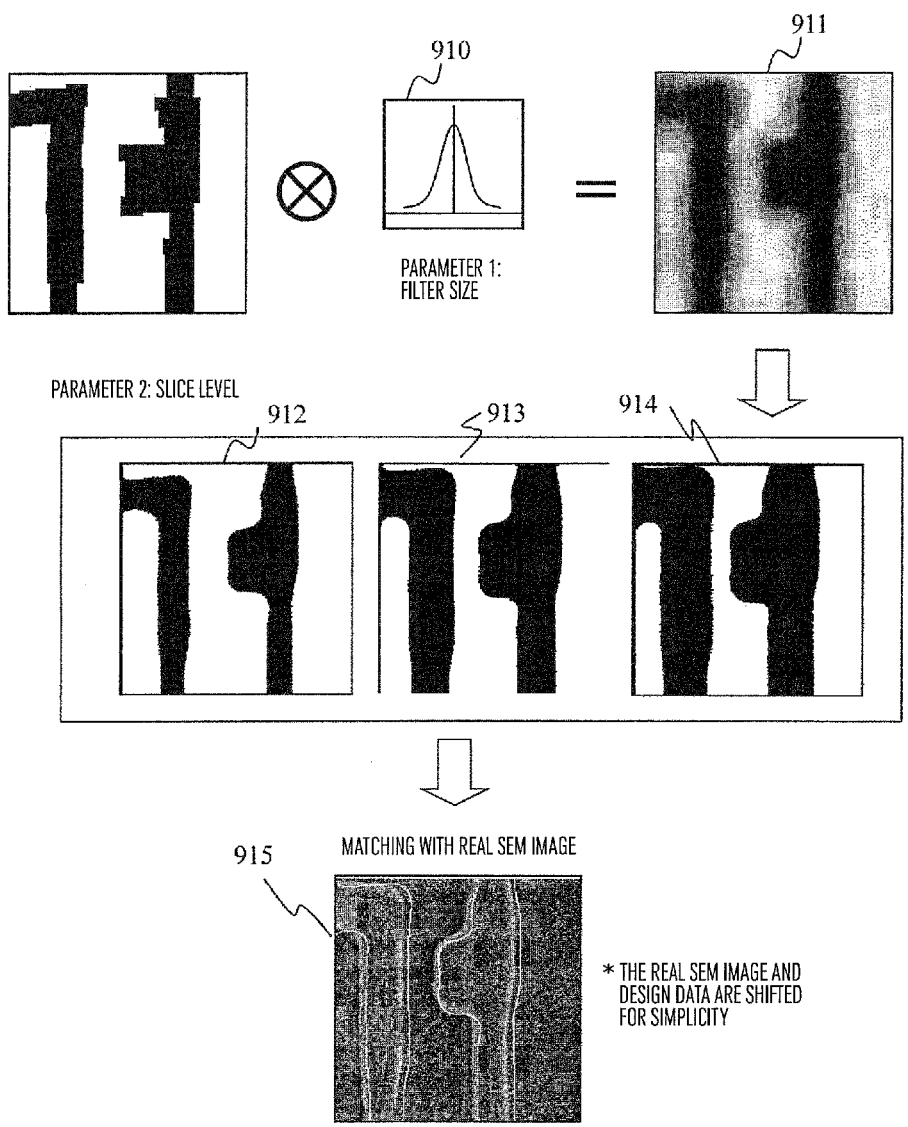
FIG. 19 is a diagram showing a design data conversion method when mask pattern data is used in the second embodiment of the present invention.

Next, FIG. 19 shows the preprocessing that is performed when a mask pattern (FIG. 17(b)) is used. OPC (optical proximity correction) has been performed on the mask pattern, and the preprocessing, which simulates exposure simulation, must be performed. First, a multivalued image 911, which has brightness gradient on the edge portion, is generated by convoluting a blur function 910 (such as Gaussian function) into the mask pattern. After that, a plurality of binarized patterns (912-914) are generated by varying the slice level, and the two parameters, a blur filter size 910 and the slice level, are optimized so that they match the real pattern. As with the rounding processing, the pattern with the maximum correlation coefficient between the real SEM image and the processed image is selected or the pattern is determined through visual observation (915).

Figure 20:
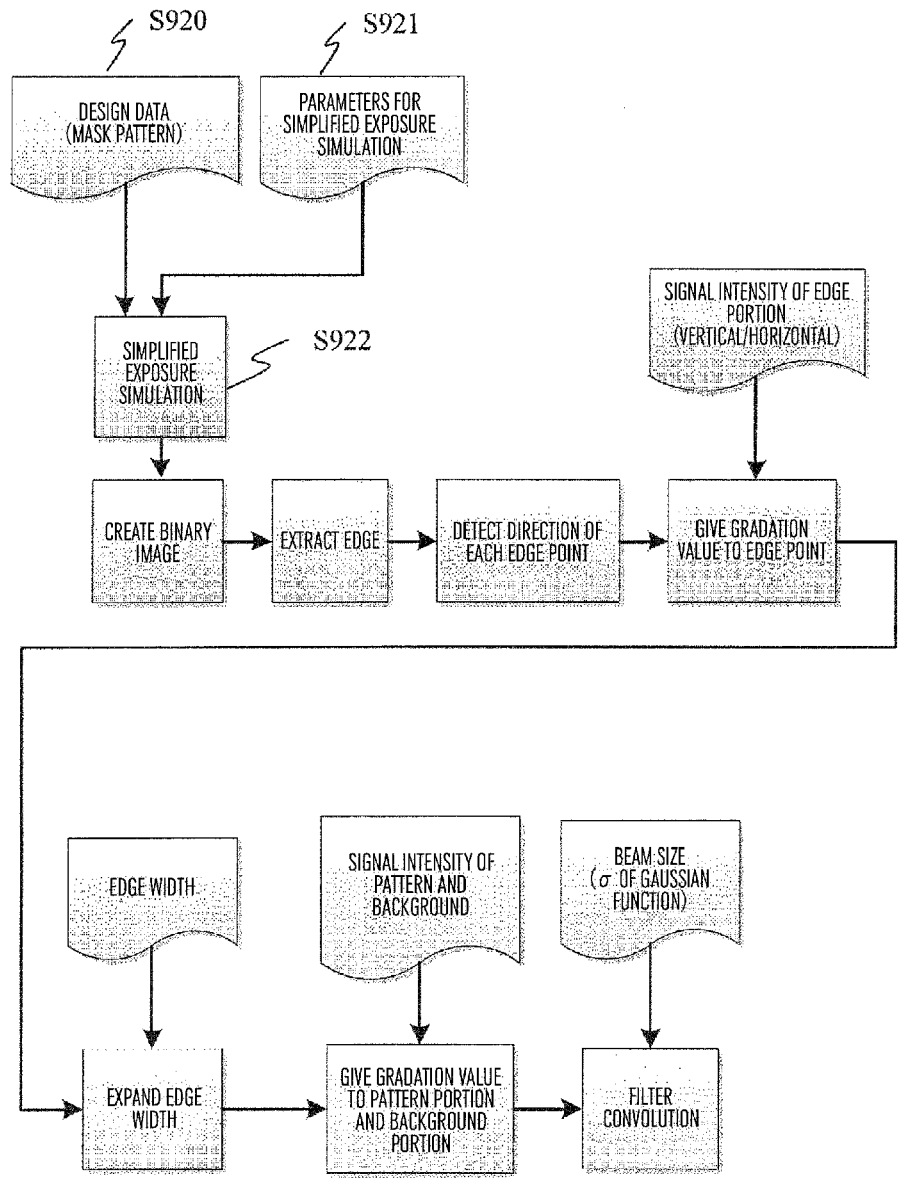
FIG. 20 is a diagram showing a flow of simulated SEM image generation processing when mask pattern data is used in the second embodiment of the present invention.

FIG. 20 shows a simulated SEM image generation flow in the second embodiment that corresponds to the simulated SEM image generation flow in the first embodiment shown in FIG. 10. With the design data (mask pattern) and the simplified exposure simulation parameters (blur filter size, slice level), determined as described above, as the input (S920, S921), simplified exposure simulation, that is, binarization based on blur filter convolution and specified slice levels, is performed (922). The subsequent processing is similar to that shown in FIG. 10.

Because exposure simulation generally requires a huge amount of time, the inspection device user has not always performed exposure simulation for the whole die area. According to the second embodiment described above, the applicable range is expanded in the sense that the D2DB inspection can be implemented when the design data owned by the inspection device user is any one of a design intent or a mask pattern. In addition, when comparing the data amount among various types of design data, the more the number of vertices of a design pattern is, the larger the data amount is. Therefore, the data amount is in the order of design intent<mask pattern<lithography simulation. This embodiment uses smaller-amount design data, thus providing the advantage in the time required for data transfer and the memory capacity required for storing data.

Third Embodiment

Figure 21:
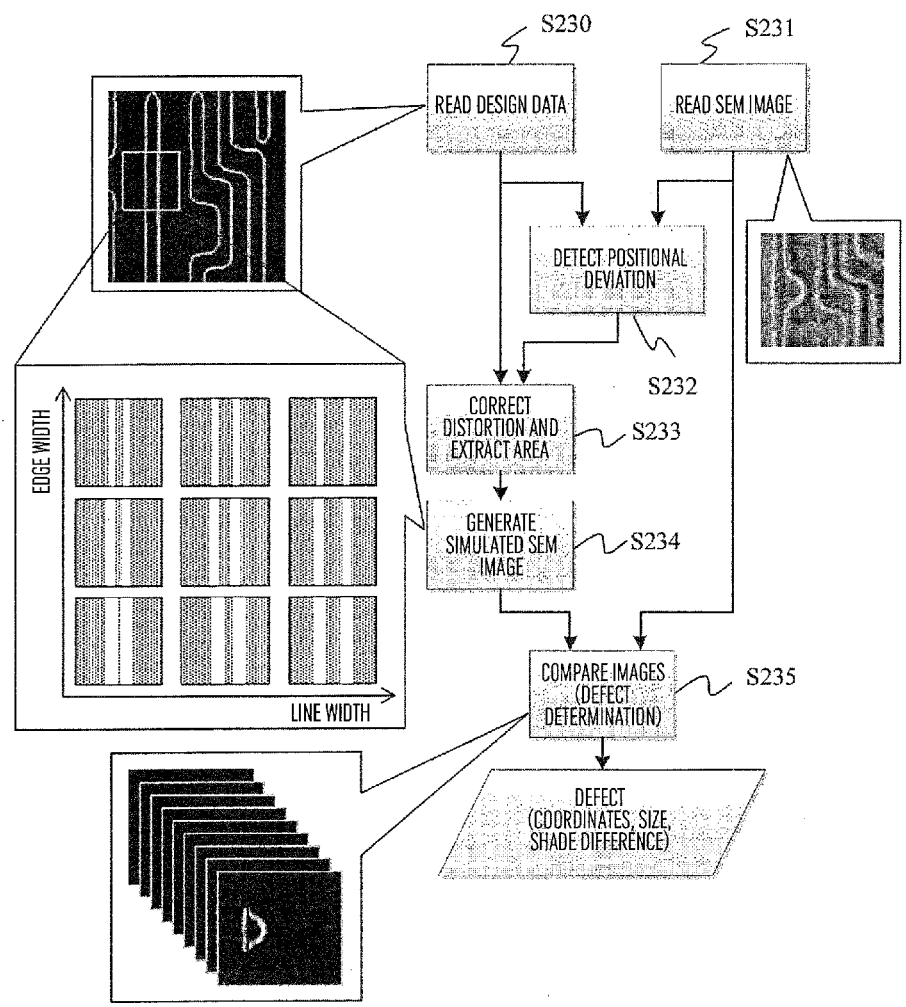
FIG. 21 is a diagram showing a flow of shade comparison, which allows for a process variation, in a third embodiment of the present invention.

FIG. 21 shows a third embodiment. The flow in FIG. 21 is similar to the flow in FIG. 3 in the first embodiment except that there is a plurality of simulated SEM images.

The reading of design data (S230), the reading of a SEM image (S231), the detection of a positional deviation (S232), and distortion correction and extraction (S233) are the same as those in the first embodiment. When generating a simulated SEM image in step S234, a plurality of simulated SEM images, different with each other in the pattern width (horizontal axis in the figure) and in the edge width (vertical axis in the figure, w in FIG. 7(b)), is generated. The image comparison (S235) is performed with the plurality of simulated SEM images and, only when a defect is detected in all comparisons, the defect information is output. In other words, if no defect is detected in at least one comparison, no defect information is output.

This method allows for a variation in the semiconductor process. That is, the purpose is to reduce an error in the inspection accuracy that may be caused by a variation in the semiconductor process. For example, when the exposure amount of the exposure device is increased or decreased in the semiconductor exposure process, the pattern width is increased or decreased. Similarly, when the focus of the exposure device varies, the edge width is increased or decreased. When the semiconductor process state differs between the wafer used for calculating the parameters for generating a simulated SEM image and the wafer to be inspected, the pattern width or the edge width differs between the simulated SEM image and the real SEM image, resulting in a defect in the whole area. This result, though correct if a change in the line width or the edge width is detected as a defect, is inconvenient when detecting a decrease or an increase in a local pattern. The purpose of this embodiment is to avoid this problem.

According to this embodiment, a pattern width change in the whole area or a gently-rising edge in the whole area, which may be caused by a process variation, is not detected as a defect, but only a local shape change can be detected.

Although the pattern width and the edge width are used as parameters for generating a plurality of simulated SEM images in the above description, only one of them may be used or another shape parameter (rounding of a corner, a recession in a pattern tip, etc.) may be changed. It is desirable for the user to set the parameter variation range before the inspection in the sense that the upper limit of the allowance amount of a process variation is set.

Fourth Embodiment

Figure 22:
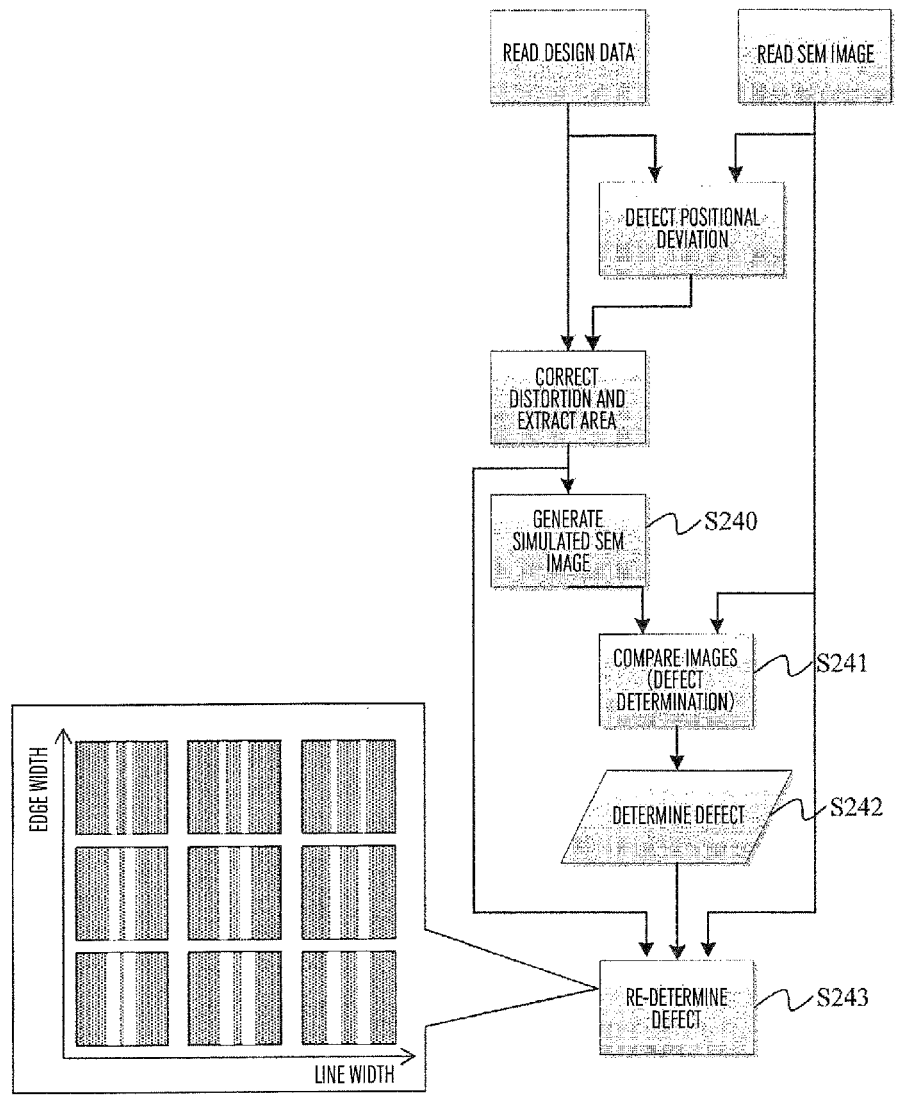
FIG. 22 is a diagram showing a flow of shade comparison, which allows for a process variation, in a fourth embodiment of the present invention.

FIG. 22 shows a fourth embodiment. As with the third embodiment, the purpose of the fourth embodiment is to allow for a process variation.

In this embodiment, a plurality of simulated SEM images is not generated in step S240 but one type of simulated SEM image is used in the comparison for defect determination (S241, S242). For a portion determined as defective, the design data corresponding to the real SEM image is saved and is compared with a plurality of simulated SEM images in the defect re-determination processing (S243). The defect re-determination processing may be performed either in synchronization with the inspection or later using the saved data.

This embodiment, in which the inspection sensitivity can be freely changed later, is convenient when it is difficult to set the allowance amount of a process variation in advance. This embodiment is also convenient for analyzing a change in the occurrence of a defect when the allowance amount of a process variation is changed.

Fifth Embodiment

Figure 23:
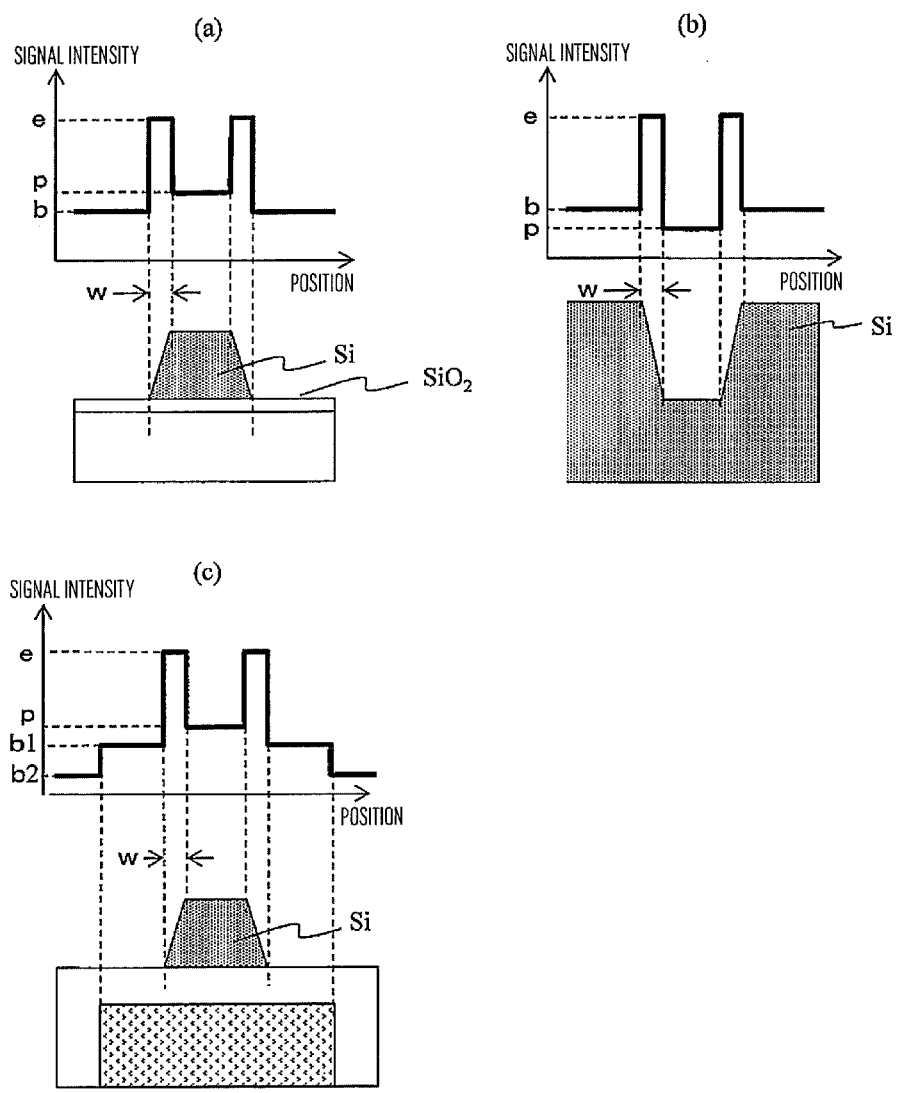
FIG. 23 is a diagram showing a method for modeling a SEM image other than a resist pattern in a fifth embodiment of the present invention.

FIG. 23 shows a fifth embodiment. A resist pattern is inspected in the first embodiment as shown in FIG. 6, while a non-resist pattern is inspected in the fifth embodiment.

FIG. 23(a) shows an inspection in which a silicon pattern is inspected, and FIG. 23(b) shows an inspection in which a silicon trench is inspected. In this case, too, the modeling method is basically similar to that in FIG. 6, with a SEM image represented by three types of signal intensity, i.e., the signal intensity of the pattern portion, the signal intensity of the edge portion, and the signal intensity of the background portion. FIG. 23(c) shows a case in which a pattern is included in the bottom layer. Because there are two types of signal intensity for the background in this case, the SEM image is represented by a total of four types of signal intensity. For calculating the simulated SEM image generation parameters, the same method as that in the first embodiment can be used.

According to this embodiment, the inspection method is applicable not only to a resist pattern but also to the systematic defect inspection of the processes of semiconductor patterning such as a gate pattern, a wiring pattern, and an STI pattern.

Sixth Embodiment

Figure 24:
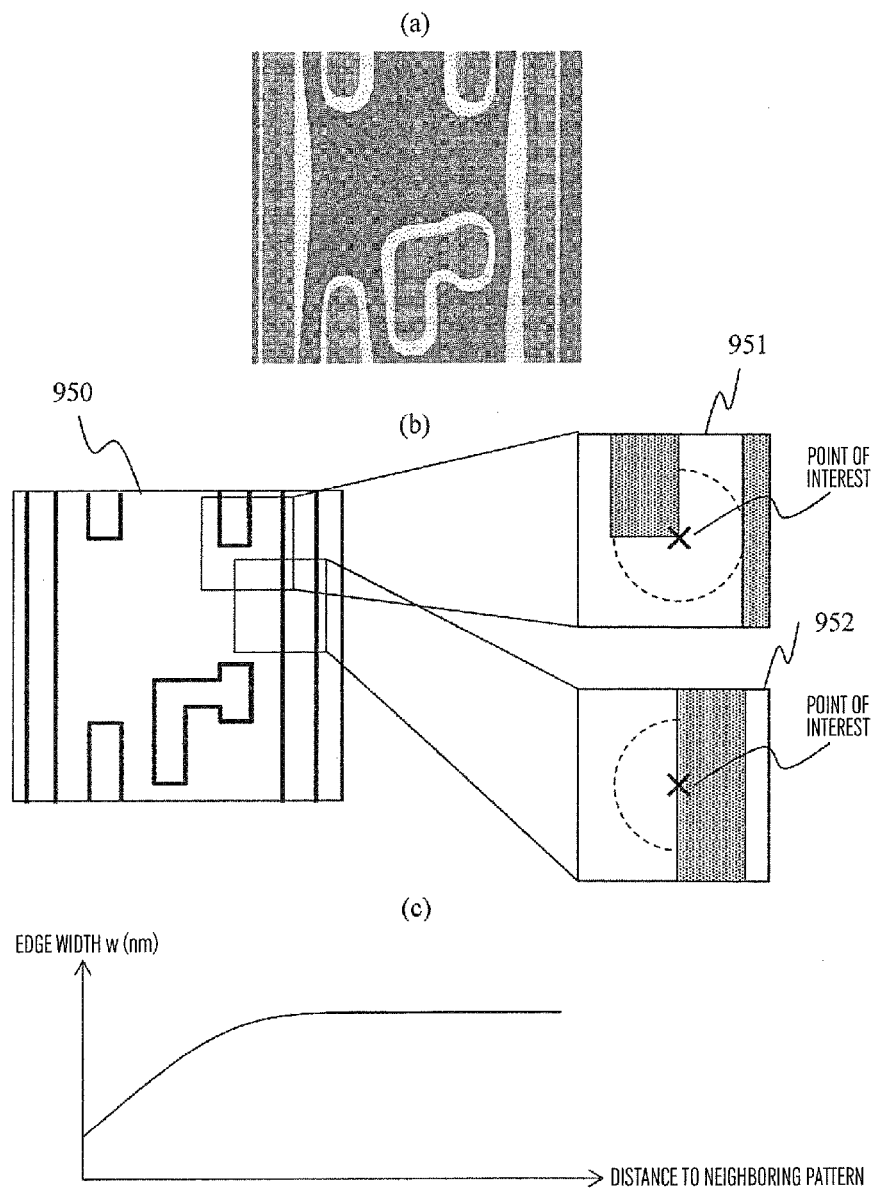
FIG. 24 is a diagram showing a method for modeling a SEM image considering pattern density in a sixth embodiment of the present invention.

FIG. 24 shows a sixth embodiment. In this embodiment, modeling is performed in more detail than in the modeling of a SEM image (FIG. 6) in the first embodiment. FIG. 24(a) is a diagram showing the simulation of the SEM image of a resist pattern. When the wavelength of an exposure light for patterning a resist becomes smaller than the pattern width of the resist, the taper angle of the pattern edge becomes varied due to the optical proximity effect. FIG. 24(a) shows the edge portion as a light zone. As shown in the figure, a high pattern density tends to cause the edge to rise perpendicularly (narrower edge width in the image), and a low pattern density tends to cause the edge to rise gently (wider edge width in the image), in many cases. In this embodiment, design data 950 is used as shown in FIG. 24(b) and, for each point of interest, the distance to the neighboring pattern is calculated (the result is that the distance indicated by the reference numeral 952 is longer than the distance indicated by the reference numeral 951). The lookup table (FIG. 24(c)), which represents the relation between the distance to the neighboring pattern and the edge width, is referenced to find the edge width.

In the first embodiment, modeling is simple because all edge widths are equal as shown in FIG. 7. In the sixth embodiment, the edge width varies according to the distance to the neighboring pattern. When the imaging magnification of an image is low, there is no practical problem with the simple modeling in which the edge width is a fixed value. However, when the imaging magnification is high, it is desirable to apply this embodiment for high-accuracy inspection.

Seventh Embodiment

Figure 25:
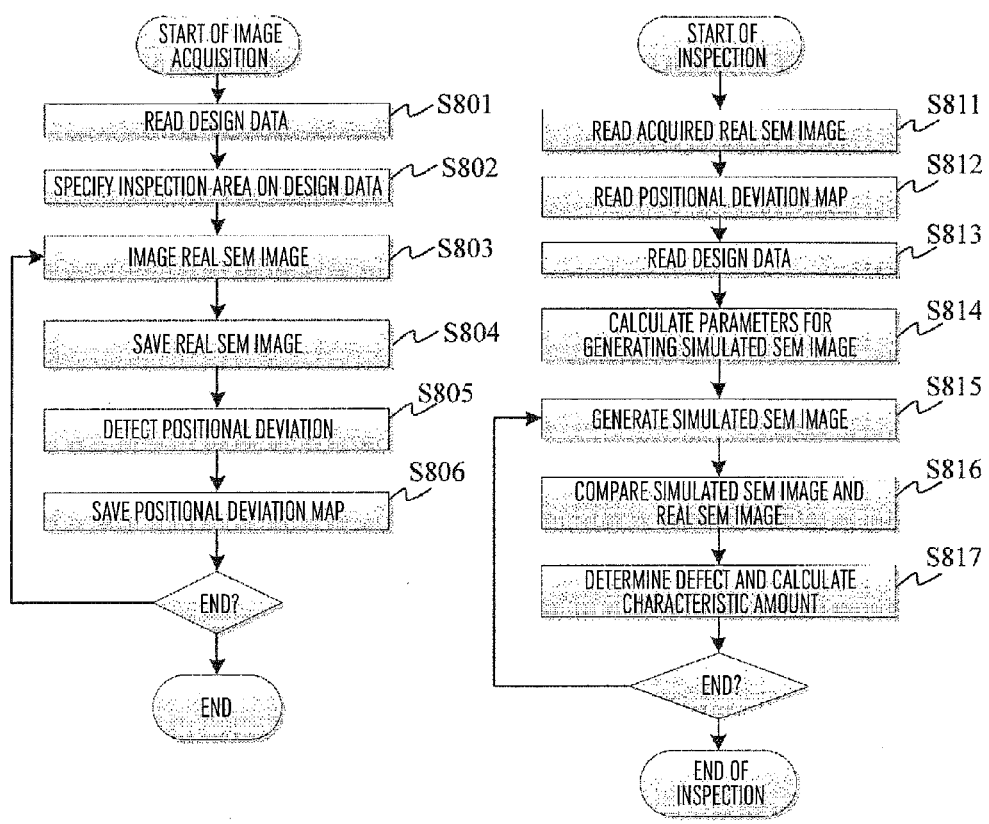
FIG. 25 is a diagram showing an overall flow of a method for later calculating parameters for simulated SEM image generation in a seventh embodiment of the present invention.

FIG. 25 shows an overall flow in a seventh embodiment. In the first embodiment (FIG. 1), the parameters for generating a simulated SEM image are determined before the inspection. In the seventh embodiment, the image of an inspection area is imaged first and then saved and, later, the saved image and the design data are compared for inspection.

FIG. 25(a) shows a flow of the imaging of an image. First, the design data is read (S801) and an inspection area is specified on the design data (S802). The SEM image of the specified area is imaged (S803), and the imaged image is saved (S804). As in step S523 in FIG. 1, a positional deviation is detected (S805), a positional deviation map (similar to the one indicated by the reference numeral 206 in FIG. 3) is calculated, and the calculated positional deviation map is saved (S806).

FIG. 25(b) shows a flow of inspection performed through comparison between the imaged image and the design data. Because imaging is already completed, the subsequent flow may be performed on the inspection device or on a computer installed outside the inspection device.

First, the saved SEM image, positional deviation map, and design data are read (S811, S812, S813). After that, the parameters for generating the simulated SEM image are calculated using the imaged SEM image (S814). The method is similar to that in step S513 in the first embodiment. The simulated SEM image is generated using the calculated parameters (S815) and is compared with the inspection image (S816) for determining a defect and for calculating the characteristic amount of the defective portion (S817).

This embodiment, in which parameter setting is performed using the inspection image to be used in the actual inspection, is more advantageous than the first embodiment from the viewpoint of parameter accuracy. However, when the inspection area is large (for example, when inspecting the whole area of one die), it is difficult to save all images. Therefore, this embodiment is efficient when the inspection area is small. It is also possible to store all images of a defective portion by performing the inspection according to the flow in FIG. 1 and, for that image, to perform re-inspection according to the flow in FIG. 25(b). In this case, defect candidate areas are calculated according to the flow in FIG. 1, and an area is selected from the defect candidate areas according to the flow in FIG. 25(b).

Eighth Embodiment

Figure 26:
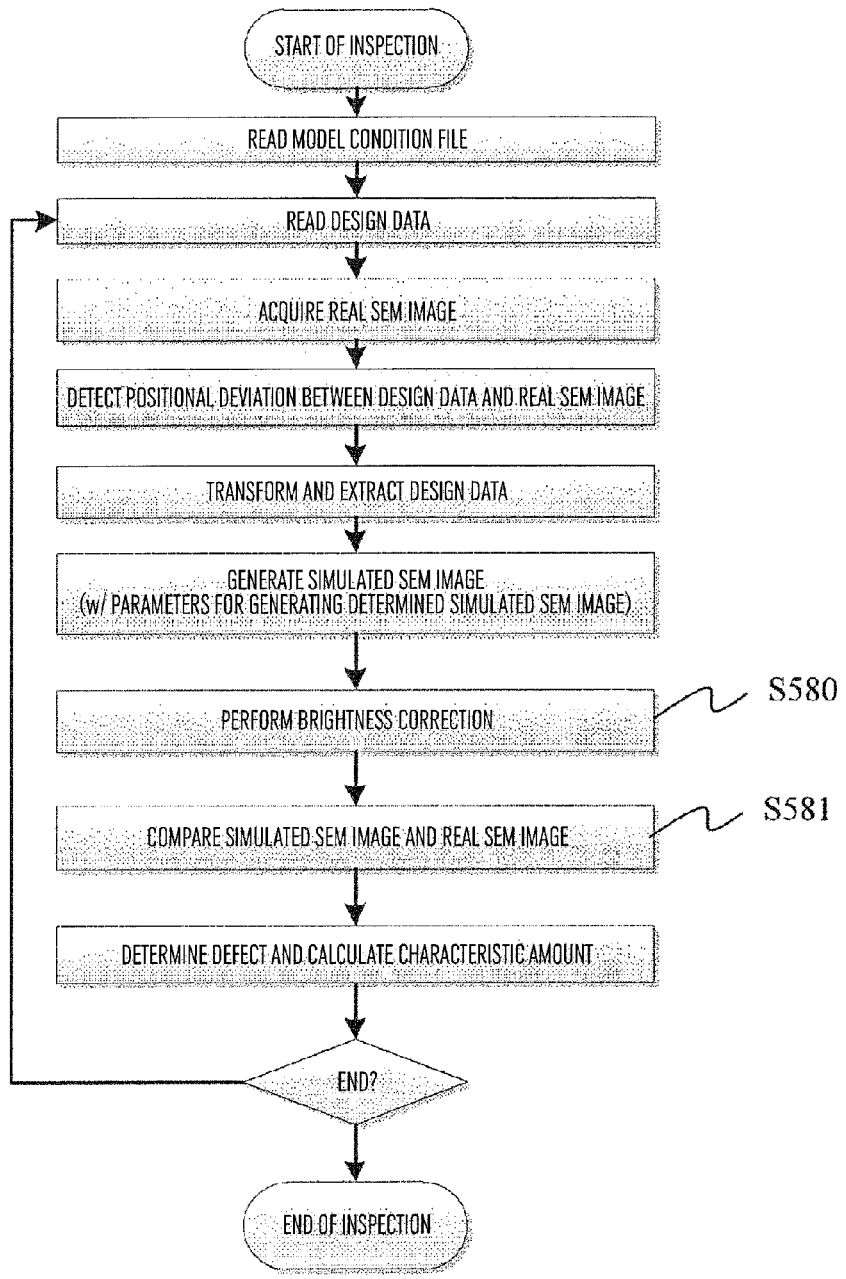
FIG. 26 is a diagram showing a flow of inspection, in which brightness correction is included, in an eighth embodiment of the present invention.

FIG. 26 shows a flow in an eighth embodiment. The eighth embodiment is similar to the first embodiment except that step 580 of brightness correction is added to the inspection flow in the first embodiment (FIG. 1(b)).

The condition setting, which is performed before the inspection, is the same as that in the first embodiment shown in FIG. 1(a). In the first embodiment, the simulated SEM image, generated by applying the simulated SEM image generation parameters determined in the flow shown in FIG. 1(a), is used directly in comparison inspection (step S526 in FIG. 1). On the other hand, in the eighth embodiment, comparison inspection (S581) is performed after the brightness of the whole image is corrected (S580).

Figure 27:
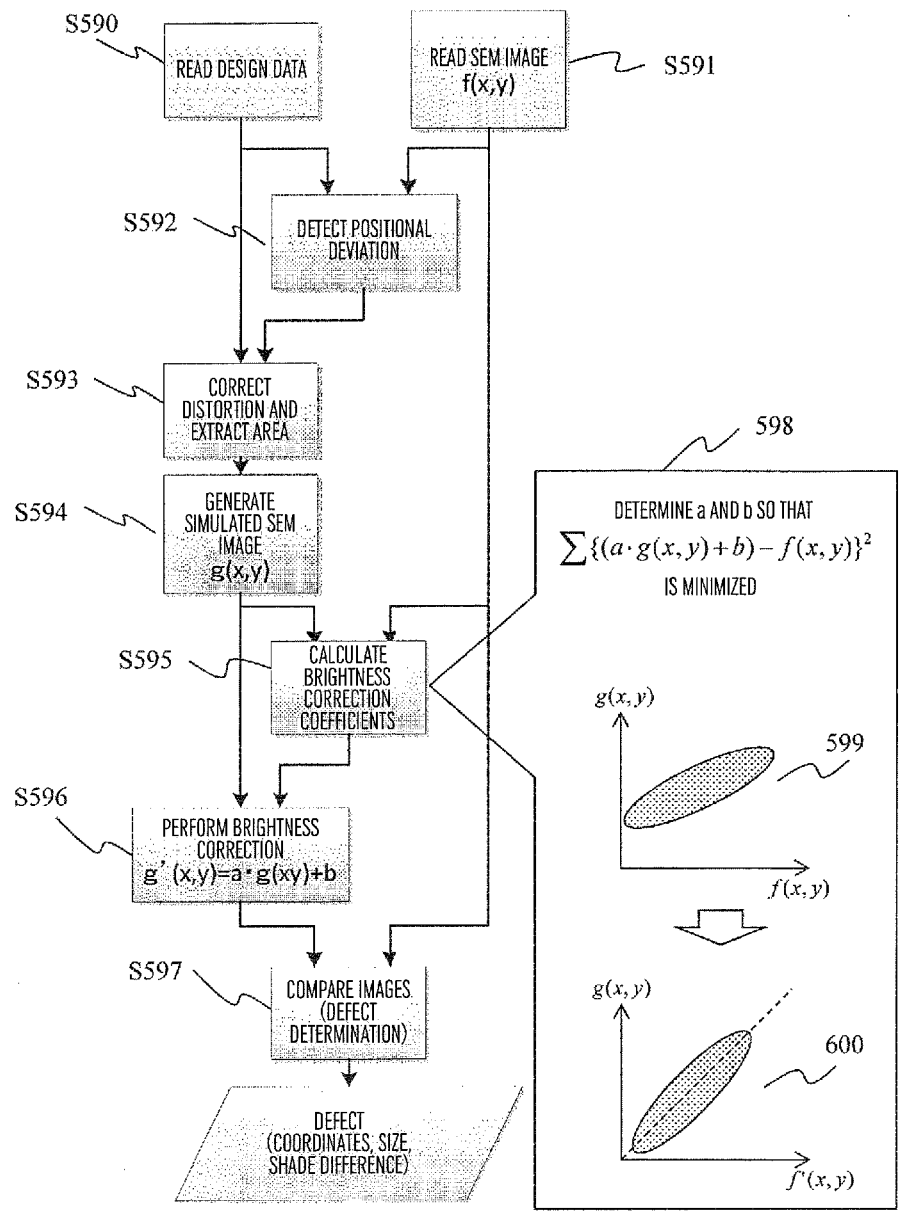
FIG. 27 is a diagram showing a method for correcting brightness in the eighth embodiment of the present invention.

FIG. 27 shows a defect determination flow in this embodiment that corresponds to the defect determination flow (FIG. 3) in the first embodiment. The steps for the reading of design data (S590), reading of a SEM image (S591), detection of a positional deviation (S592), correction and extraction of a distortion (S593), and generation of a simulated SEM image (S594) are the same as those in the first embodiment.

After these steps, the brightness correction coefficient is calculated (S595). Let the real SEM image be f(x, y), and let the simulated SEM image be g(x, y). The coefficients a and b are determined in such a way that the sum of squares (expression (8)) of the difference between the image, generated by multiplying the simulated SEM image by a and then adding b to the result, and the real SEM image is minimized (598).

(MATH. 8)

$$\Sigma\{(a \times g(x,y)+b)-f(x,y)\}^2 \quad \text{(Expression 8)}$$

After that, the simulated SEM image is converted to find g'(x, y) using expression (9). Image comparison is performed between the converted simulated SEM image g'(x, y) and the real SEM image f(x, y).

(MATH. 9)

$$g'(x,y)=a \times g(x,y)+b \quad \text{(Expression 9)}$$

The bright correction (S596), performed as described above, produces the following result. Before the correction, there is a brightness deviation between f(x, y) and g(x, y) as in the distribution diagram indicated by the reference numeral 599 (the points are plotted in the diagram where the horizontal axis indicates the brightness of the coordinates (x, y) of f(x, y) and the vertical axis indicates the brightness of the corresponding coordinates of g(x, y)). After the correction, the distribution diagram changes to the one, indicated by the reference numeral 600, where the points distributed around the line y=x.

In some cases, the device state changes between the time when the parameters for simulated SEM image generation are calculated and the time when the inspection is made, with the result that the state indicated by the reference numeral 599 is generated. In this case, the image comparison (S597) between f(x, y) and g(x, y) using expression (1) will generate an incorrect result in many cases. This embodiment, in which the brightness correction is performed, avoids this problem. The correction coefficients, which are calculated in such a way that the brightness match is achieved, not a local brightness basis, but on a whole image brightness basis, prevent a defective portion from being overlooked.

The conversion processing, though performed for the simulated SEM image in the description above, may be performed for the real SEM image.

In addition to the case in which the device state changes as described above, this embodiment is applicable also to the case in which the brightness changes on a whole image basis because the wafer, used for calculating the parameters for generating the simulated SEM image, and the wafer to be inspected are different.

Ninth Embodiment

The ninth embodiment is an additional function of the eighth embodiment. In the eighth embodiment, the brightness correction coefficient is calculated for each image. On the other hand, in this embodiment, the past brightness correction coefficients are referenced to calculate the current brightness correction coefficient in order to calculate the brightness correction coefficient more reliably.

FIG. 28 is a diagram in which the points are plotted with the time t on the horizontal axis and the brightness correction coefficient a on the vertical axis. Because the patterns included in the acquired images differ with each other, the brightness correction coefficient 'a' calculated for each image includes an error to some extent with the result that the plotted points are distributed as indicated by the reference numeral 850. In this embodiment, the brightness coefficient A(t) to be used for the current time t is determined by (expression 10)

using the past brightness correction coefficients, where a(t) is the brightness correction coefficient at the current time t.

(MATH. 10)

$$A(t) = (a(t) + A(t-1) + A(t-2))/3 \quad \text{(Expression 10)}$$
$$= \{a(t) + (a(t-1) + a(t-2) + a(t-3))/3 +$$
$$(a(t-2) + a(t-3) + a(t-4))/3\}/3$$

A(t) obtained by this calculation is a smooth curve as indicated by the reference numeral 851. Using A(t) instead of a(t) allows the brightness correction coefficient to be calculated more reliably, resulting in an increase in the accuracy of the inspection. For example, when an image includes a large defect, the brightness correction coefficient calculated in the eighth embodiment is affected by the large defect. In this case, the ninth embodiment, if used, reduces this problem.

The brightness correction coefficient may be calculated by simply using (expression 10), or irregular data may be deleted from the calculation by detecting an irregularity in the correction coefficients. Although the brightness correction coefficient a is described as an example above, the same processing may of course be performed for b.

Tenth Embodiment

Figure 29:
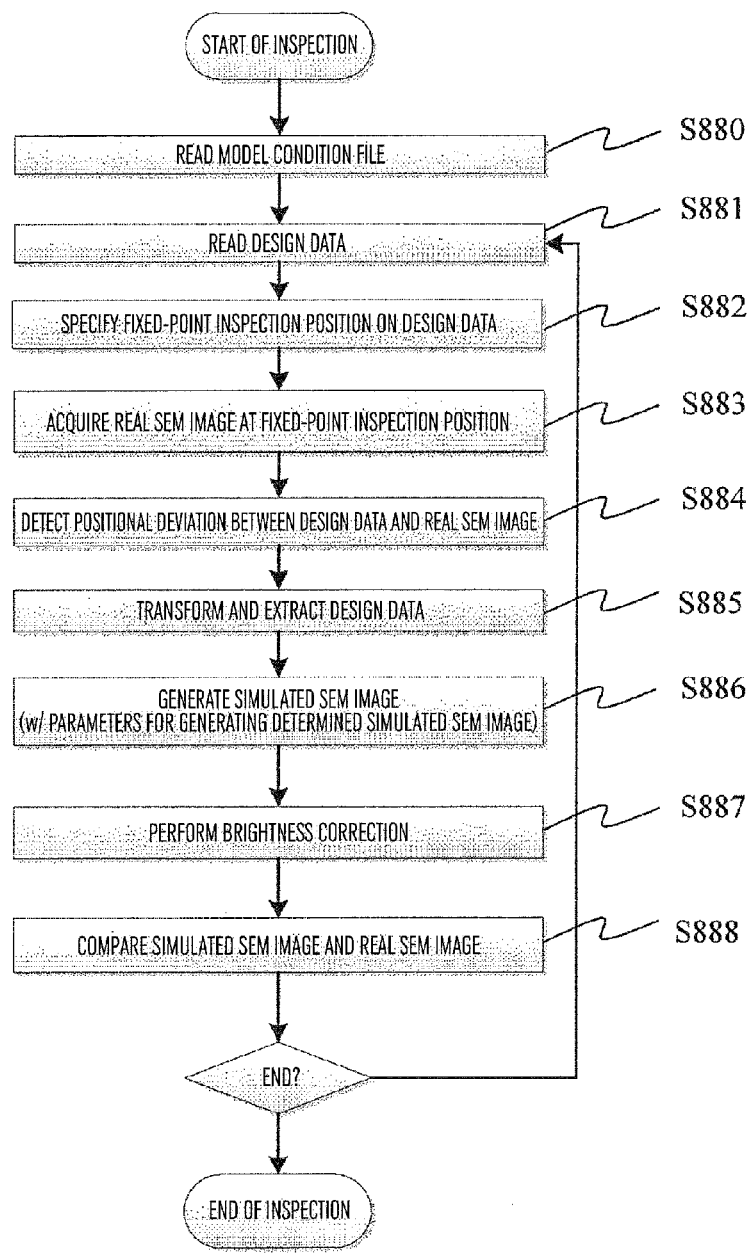
FIG. 29 is a diagram showing a flow of fixed-point inspection in a tenth embodiment of the present invention.

FIG. 29 shows a flow in a tenth embodiment. In the first embodiment, an inspection is made for a relatively large area for locating a defect; on the other hand, in the tenth embodiment, a fixed-point inspection is made for inspecting only a specified area.

The condition setting, which is performed before the inspection, is the same as that in the first embodiment (FIG. 1(*a*)). FIG. 29 shows a flow corresponding to the flow in FIG. 1(*b*) in the first embodiment.

First, the model condition file and the design data are read (S880, S881) and a position, where a fixed-point inspection is to be made, is specified on the design data (S882). The position, where a fixed-point inspection is to be made, is a point determined by the process simulation as a possible defective position or a point where a defect was frequently generated in the past inspections. Next, the real SEM image of the specified position is acquired (S883), a positional deviation between the design data and the real SEM image is detected (S884), and the design data is transformed and extracted based on the positional deviation detection result (S885). After that, as in the first embodiment, the parameters described in the model condition file that is read in step S880 are applied to generate a simulated SEM image (S886). In the next step S887 where brightness correction is performed, the method described in the eighth embodiment is applied. After that, the inspection is performed by comparing the simulated SEM image, for which brightness correction has been made, with the real SEM image (S888).

Figure 30:
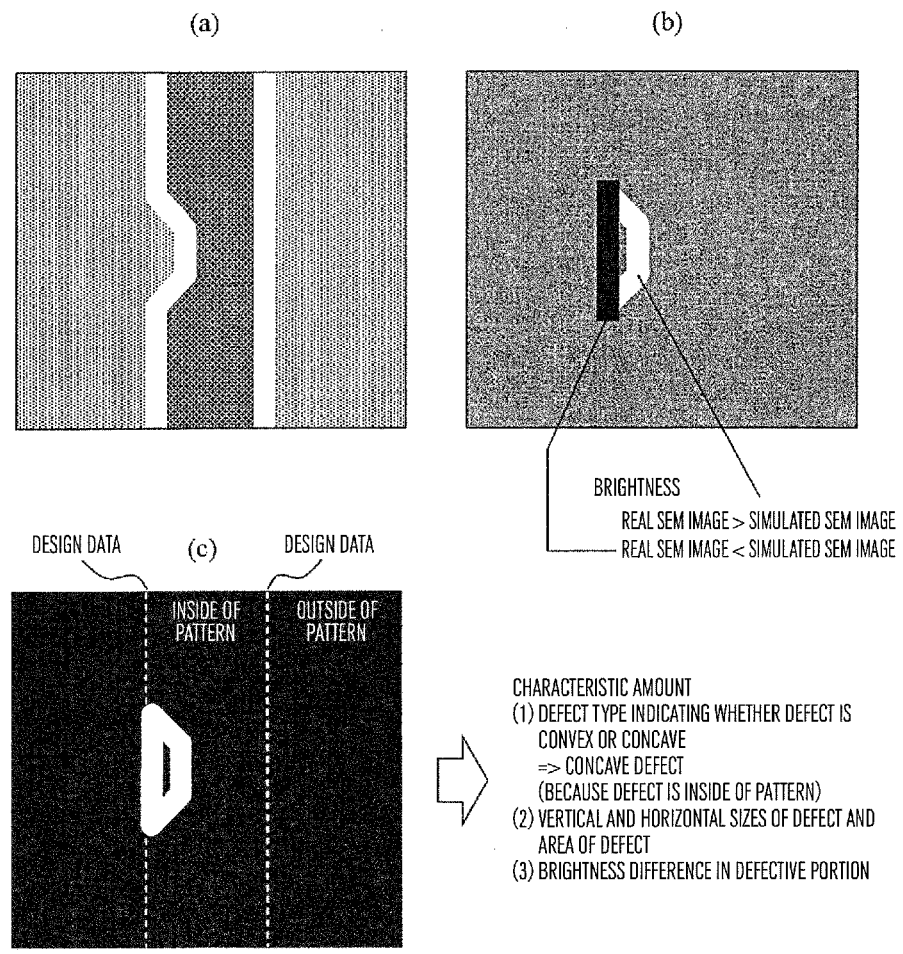
FIG. 30 is a diagram showing the evaluation values output as an inspection result of the fixed-point inspection in the tenth embodiment of the present invention.

FIG. 30 shows an output example of a fixed-point inspection. FIG. 30(*a*), a schematic diagram of a real SEM image, shows a line pattern that has a concave defect (partially thinned line) in an intermediate position. The difference between this image and the simulated SEM image is as shown in FIG. 17(*b*). As shown in the figure, the brightness in the difference image differs according to whether the brightness of the real SEM image is higher than that of the simulated SEM image or the brightness of the real SEM image is lower than that of the simulated SEM image.

The output of a defect includes the defect type (concave defect or convex defect) determined according to whether the defective portion is inside or outside of the design pattern, the vertical and horizontal sizes of the defect, the area of the defect, or the brightness difference in the defective portion.

According to this embodiment, a comparison with a simulated SEM image can be performed in a fixed-point inspection. By comparing with a simulated SEM image, a quantitative evaluation can be made not only for a defect occurring as a difference in the shape as described above but also for a defect occurring as a difference in the brightness such as a thin-film remnant.

Eleventh Embodiment

An eleventh embodiment relates to the setting of a threshold for defect determination. In the first embodiment, an image is determined as defective if the shade difference between a real SEM image and a simulated SEM image is equal to or larger than a fixed value as shown in (MATH. 1); on the other hand, in this embodiment, a threshold is set according to the brightness g(x, y) of a simulated SEM image.

The characteristic of a SEM image is that the brighter the image is, the higher the noise is (characteristic of a shot noise). Therefore, an incorrect determination or a defect-detection failure can be reduced by setting a smaller defect-determination threshold for a dark portion, and a larger defect-determination threshold for a bright portion.

Figure 31:
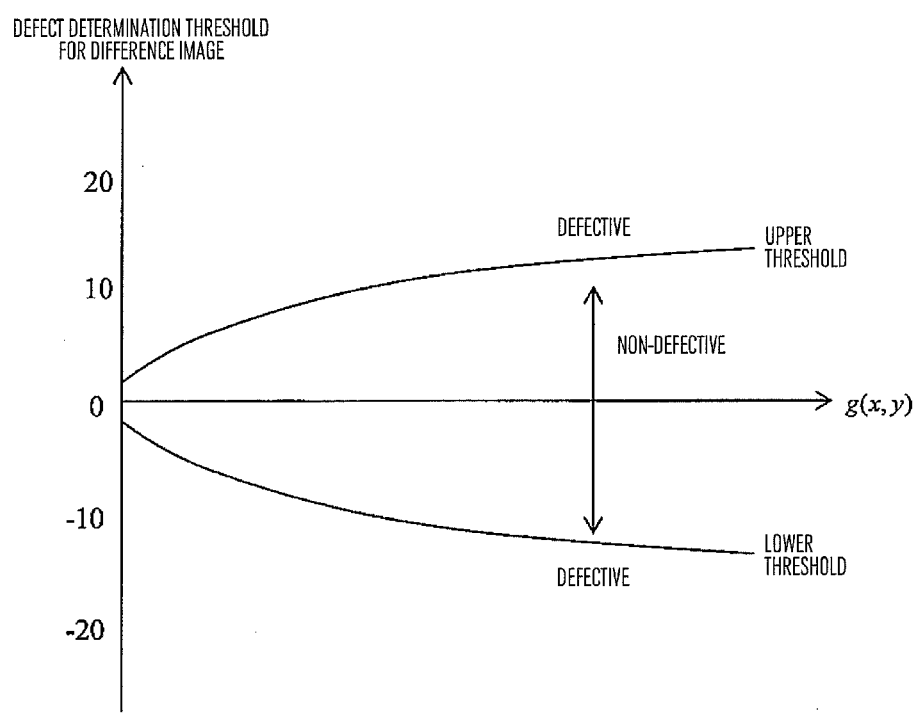
FIG. 31 is a diagram showing a method for calculating defect determination values in an eleventh embodiment of the present invention.

In this embodiment, a lookup table, which represents the relation between the brightness of the simulated SEM image and defect determination thresholds, is created before the inspection as shown in FIG. 31. At inspection time, this lookup table is referenced for defect determination.

The point here is that the brightness of a simulated SEM image is used to reference the lookup table. Instead, if the brightness of a real SEM image is used, the brightness of a defective portion is used to reference the lookup table for a defective portion, possibly preventing the intended purpose of performing an inspection using noise characteristics from being achieved. In this embodiment, the brightness of the simulated SEM image is used to reference the lookup table to achieve the intended purpose.

This embodiment enables a high-accuracy inspection with the effect of a SEM noise minimized.

Twelfth Embodiment

A twelfth embodiment relates to positional deviation detection.

Figure 32:
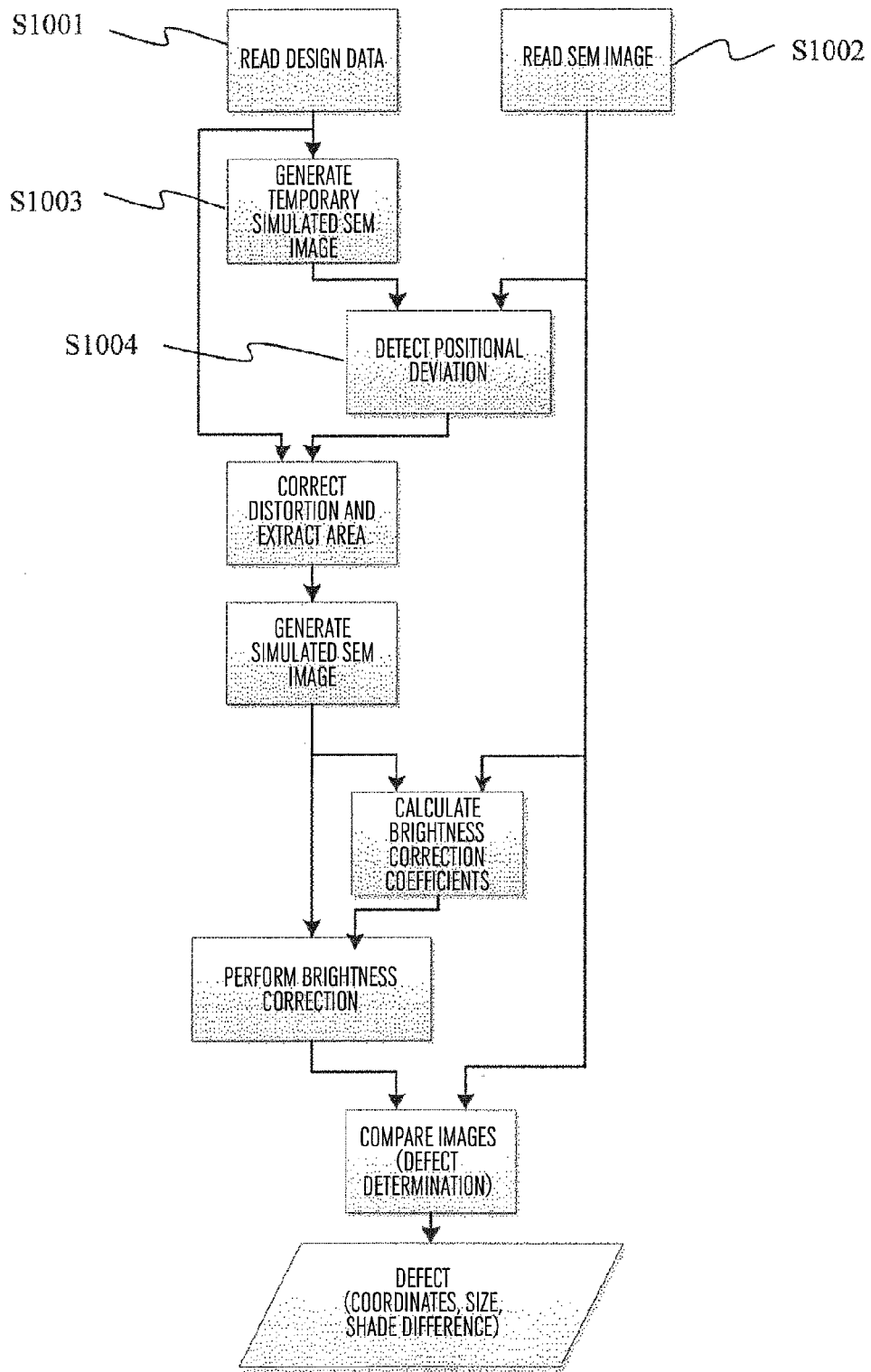
FIG. 32 is a diagram showing a method for using a simulated SEM image in detecting a positional deviation in a twelfth embodiment of the present invention.

In the first embodiment, the design data and the real SEM image are used to detect a positional deviation (S205) as shown in FIG. 3. In the twelfth embodiment, the design data is read (S1001), a simulated SEM image is generated from this design data (S1003, the parameters for generating the simulated SEM image are read from the model condition file not shown), and a positional deviation detection is performed (S1004) between the generated simulated SEM image and the real SEM image that is read (S1002) as shown in FIG. 32. The subsequent processing is similar to that in the first embodiment.

In general, the accuracy of positional deviation detection is increased by performing positional deviation detection between the images with similar characteristics.

This embodiment increases the accuracy of positional deviation detection and increases the accuracy of distortion correction and extraction in the subsequent stages, resulting in an increase in inspection performance.

Thirteenth Embodiment

A thirteenth embodiment relates to the acquisition of a real SEM image. In the description of the SEM image acquisition method in the first embodiment, one of the following two types of images, continuous image and a sheet image, is inspected. A continuous image is an image obtained by the one-dimensional scanning of an electron beam and the continuous movement of the stage, and a sheet image is an image obtained by the two-dimensional scanning of an electron beam and the step movement of the stage. As shown in FIG. 3, the stage movement direction and the beam scanning direction may be tilted.

FIG. 33(a) shows a method in which the stage is moved in parallel to the chip layout on a wafer and the electron beam scanning is performed obliquely with respect to the chip layout on a wafer.

FIG. 33(b) shows a method in which both the horizontal scanning direction and the vertical scanning direction of the electron beam are tilted with respect to the chip layout on a wafer.

Most of semiconductor patterns are configured by patterns at right angles to, or parallel to, the chip layout. In an electron beam image, an edge parallel to the scanning direction of the electron beam tends to get blurred due to electrification as shown in FIG. 5. In this embodiment, because the scanning direction of the electron beam and the edge direction of a pattern are not parallel in many cases, the number of blurred edges is decreased.

When a real SEM image is acquired via oblique scanning, the simulated SEM image must also be transformed to produce a similar image. To do so, because the oblique scanning angle is known (this angle is entered via the GUI shown in FIG. 16), the simulated SEM image is transformed using the oblique scanning angle in the step of transformation and extraction of design data (S523 in FIG. 1).

According to this embodiment, it is expected that fewer edges will become blurred and therefore the inspection sensitivity will be increased.

Fourteenth Embodiment

A fourteenth embodiment relates to the electronic optical system.

Figure 2:
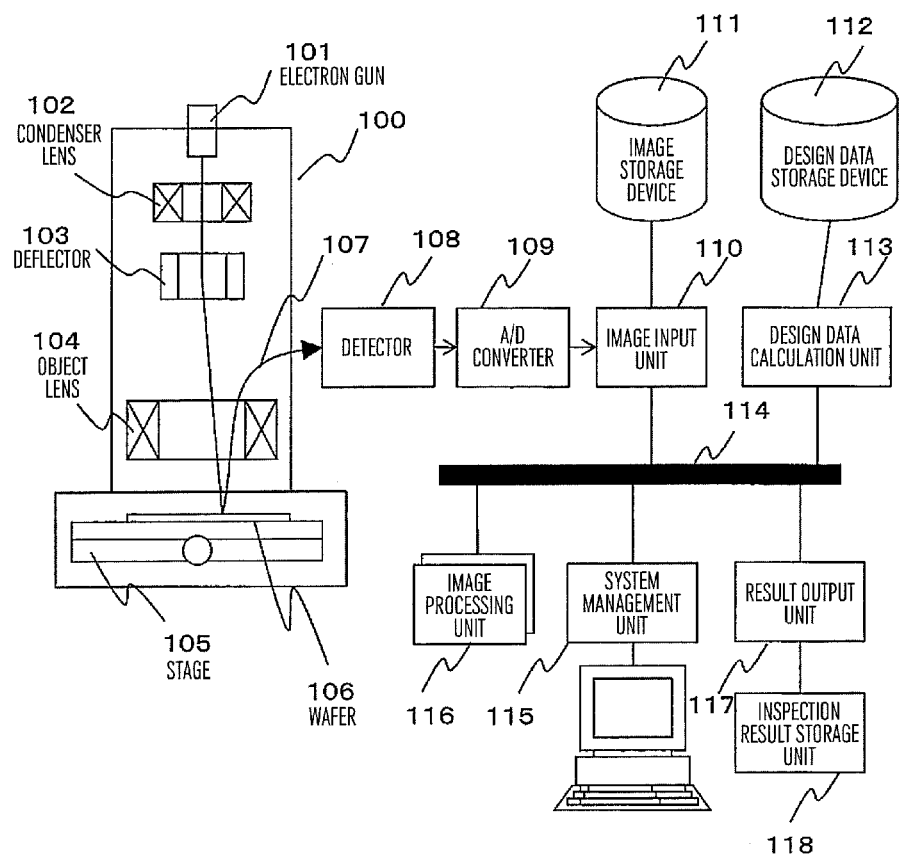
FIG. 2 is a diagram showing a system configuration in the first embodiment of the present invention.
Figure 34:
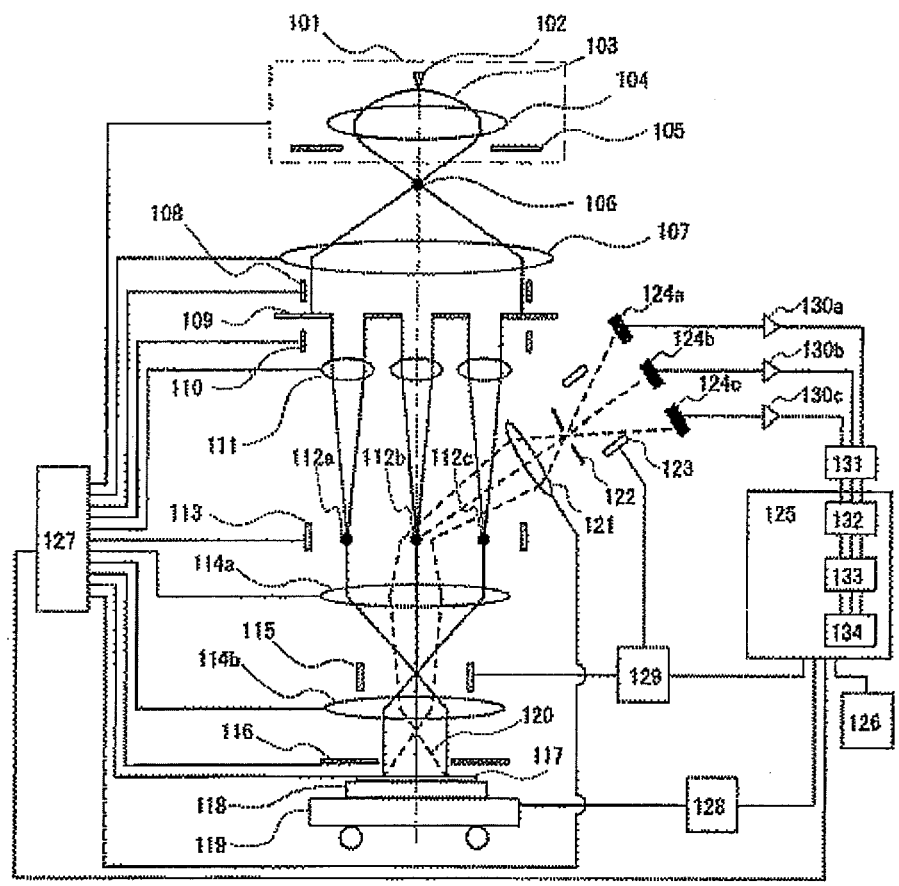
FIG. 34 is a diagram showing a multi-beam type optical system in a fourteenth embodiment of the present invention.

In the first embodiment, a single-beam optical system is used as shown in FIG. 2, On the other hand, in this embodiment, a multi-beam optical system is used as shown in FIG. 34.

Because there may be individual differences among a plurality of emitted electron beams and a plurality of detectors in the multi-beam system, the parameters for generating a simulated SEM image are calculated for each beam. In addition, it is desirable that the brightness correction described in the eighth embodiment be performed for each beam.

In this embodiment, it is expected that the inspection throughput will be increased.

The fourteen embodiments have been described. It is also possible to combine these embodiments in part or in whole.

The invention claimed is:

1. A pattern inspection device comprising:
an imaging unit that images an electron beam image of a pattern formed on a substrate;
a simulated electron beam image generation unit that generates a simulated electron beam image using a parameter based on design data, the parameter representing a characteristic of the electron beam image; and
an inspection unit that inspects the pattern on the substrate by comparing the electron beam image of the pattern and the simulated electron beam image, the electron beam image of the pattern being imaged by said imaging unit, the simulated electron beam image being generated by said simulated electron beam image generation unit.

2. A pattern inspection device comprising:
an imaging unit that images an electron beam image of a pattern formed on a substrate;
a pattern shape transformation unit that transforms a shape of the pattern using a parameter based on design data, the parameter representing a processing characteristic of the pattern;
a simulated electron beam image generation unit that generates a simulated electron beam image for the pattern using a parameter, the pattern being transformed by said pattern shape transformation unit, the parameter representing a characteristic of the electron beam image; and
an inspection unit that inspects the pattern on the substrate by comparing the electron beam image of the pattern and the simulated electron beam image, the electron beam image of the pattern being imaged by said imaging unit, the simulated electron beam image being generated by said simulated electron beam image generation unit.

3. The pattern inspection device according to claim 1, further comprising:
a condition input unit that automatically determines a parameter value, necessary for generating the simulated electron beam image, from the design data; and
a parameter calculation unit.

4. The pattern inspection device according to claim 1 wherein
the parameter representing the characteristic of the electron beam image, generated by said simulated electron beam image generation unit, include at least one of a brightness of a pattern portion, a brightness of a background portion, a brightness of an edge portion for each direction, and a blur amount of the edge portion.

5. The pattern inspection device according to claim 2, further comprising:
a variation range setting unit that sets a variation range for a parameter representing an exposure characteristic; and
a transformation pattern generation unit that generates a plurality of transformation patterns each corresponding to the variation range that is set by said variation range setting unit, wherein
said simulated electron beam image generation unit generates a plurality of simulated electron beam images corresponding to the plurality of transformation patterns generated by said transformation pattern generation unit, and
said inspection unit produces a plurality of inspection results linked to the parameter representing the exposure characteristic by comparing the electron beam image of the pattern and the plurality of simulated electron beam images, the electron beam image of the pattern being imaged by said imaging unit, the plurality of simulated electron beam images being generated by said simulated electron beam image generation unit.

6. The pattern inspection device according to claim 1, further comprising:
a variation range setting unit that sets a variation range for the parameter representing the characteristic of the electron beam image wherein said simulated electron beam image generation unit generates a plurality of simulated electron beam images, corresponding to the variation range, for the parameter representing the characteristic of the electron beam image that is set by said variation range setting unit, and said inspection unit produces a plurality of inspection results linked to the parameter representing the characteristic of the electron beam image by comparing the electron beam image of the pattern and the plurality of simulated electron beam images, the electron beam image of the pattern being imaged by said imaging unit, the plurality of simulated electron beam images being generated by said simulated electron beam image generation unit.

7. The pattern inspection device according to claim 5 wherein said variation range setting unit updates a value of the parameter representing the characteristic of the electron beam image based on a temporal transition of the plurality of inspection results that are linked to the parameter representing the characteristic of the electron beam image.

8. The pattern inspection device according to claim 1, further comprising:

a brightness adjustment unit that adjusts brightness between the electron beam image of the pattern and the simulated electron beam image; and a brightness adjustment parameter storage unit that stores a brightness adjustment parameter between the electron beam image of the pattern and the simulated electron beam image.

9. The pattern inspection device according to claim 8 wherein said brightness adjustment parameter storage unit updates a value of the brightness adjustment parameter based on a temporal transition of the stored brightness adjustment parameter.

10. A pattern inspection method comprising:

an imaging step for imaging an electron beam image of a pattern formed on a substrate;

a simulated electron beam image generation step for generating a simulated electron beam image using a parameter based on design data, the parameter representing a characteristic of the electron beam image; and an inspection step for inspecting the pattern on the substrate by comparing the electron beam image of the pattern and the simulated electron beam image, the electron beam image of the pattern being imaged by said imaging step, the simulated electron beam image being generated by said simulated electron beam image generation step.

11. A pattern inspection method comprising:

an imaging step for imaging an electron beam image of a pattern formed on a substrate;

a pattern shape transformation step for transforming a shape of the pattern using a parameter based on design data, the parameter representing a processing characteristic of the pattern;

a simulated electron beam image generation step for generating a simulated electron beam image for the pattern using a parameter, the pattern being transformed by said pattern shape transformation step, the parameter representing a characteristic of the electron beam image; and an inspection step for inspecting the pattern on the substrate by comparing the electron beam image of the pattern and the simulated electron beam image, the electron beam image of the pattern being imaged by said imaging step, the simulated electron beam image being generated by said simulated electron beam image generation step.

12. The pattern inspection method according to claim 10, further comprising:

a condition input step for automatically determining a parameter value, necessary for generating the simulated electron beam image, from the design data; and a parameter calculation step.

13. The pattern inspection method according to claim 10 wherein the parameter representing the characteristic of the electron beam image, generated by said simulated electron beam image generation step, include at least one of a brightness of a pattern portion, a brightness of a background portion, a brightness of an edge portion for each direction, and a blur amount of the edge portion.

14. The pattern inspection method according to claim 11, further comprising:

a variation range setting step for setting a variation range for a parameter representing an exposure characteristic; and a transformation pattern generation step for generating a plurality of transformation patterns each corresponding to the variation range that is set by said variation range setting step, wherein said simulated electron beam image generation step generates a plurality of simulated electron beam images corresponding to the plurality of transformation patterns generated by said transformation pattern generation step, and said inspection step produces a plurality of inspection results linked to the parameter representing the exposure characteristic by comparing the electron beam image of the pattern and the plurality of simulated electron beam images, the electron beam image of the pattern being imaged by said imaging step, the plurality of simulated electron beam images being generated by said simulated electron beam image generation step.

15. The pattern inspection method according to claim 10, further comprising:

a variation range setting step for setting a variation range for the parameter representing the characteristic of the electron beam image wherein said simulated electron beam image generation step generates a plurality of simulated electron beam images, corresponding to the variation range, for the parameter representing the characteristic of the electron beam image that is set by said variation range setting step, and said inspection step produces a plurality of inspection results linked to the parameter representing the characteristic of the electron beam image by comparing the electron beam image of the pattern and the plurality of simulated electron beam images, the electron beam image of the pattern being imaged by said imaging step, the plurality of simulated electron beam images being generated by said simulated electron beam image generation step.

16. The pattern inspection method according to claim 14 wherein said variation range setting step updates a value of the parameter representing the characteristic of the electron beam image based on a temporal transition of the plurality of inspection results that are linked to the parameter representing the characteristic of the electron beam image.

17. The pattern inspection method according to claim 10, further comprising:
- a brightness adjustment step for adjusting brightness between the electron beam image of the pattern and the simulated electron beam image; and
- a brightness adjustment parameter storage step for storing a brightness adjustment parameter between the electron beam image of the pattern and the simulated electron beam image.

18. The pattern inspection method according to claim 17 wherein
- said brightness adjustment parameter storage step updates a value of the brightness adjustment parameter based on a temporal transition of the stored brightness adjustment parameter.

* * * * *